United States Patent
Silverstone et al.

(10) Patent No.: US 12,280,068 B1
(45) Date of Patent: **\*Apr. 22, 2025**

(54) USES OF A CO-CRYSTAL OF PSILOCYBIN AND PSILOCIN

(71) Applicant: ZYLORION HEALTH INC., Calgary (CA)

(72) Inventors: Peter Silverstone, Calgary (CA); Robert Laprairie, Saskatoon (CA); Deborah Kurrasch, Calgary (CA)

(73) Assignee: Zylorion Health Inc., Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/941,779

(22) Filed: Nov. 8, 2024

Related U.S. Application Data

(60) Provisional application No. 63/597,415, filed on Nov. 9, 2023.

(51) Int. Cl.
| *A61K 31/675* | (2006.01) |
| *A61K 31/4045* | (2006.01) |
| *A61P 25/00* | (2006.01) |

(52) U.S. Cl.
CPC ........ *A61K 31/675* (2013.01); *A61K 31/4045* (2013.01); *A61P 25/00* (2018.01)

(58) Field of Classification Search
CPC .................................................. A61K 31/675
See application file for complete search history.

(56) References Cited

U.S. PATENT DOCUMENTS

| 2019/0119310 A1 | 4/2019 | Londesbrough et al. |
| 2022/0143051 A1 | 5/2022 | Manfredi et al. |
| 2023/0210872 A1 | 7/2023 | Stamets et al. |

FOREIGN PATENT DOCUMENTS

| CA | 3078765 A1 | 4/2019 |
| WO | 2021207824 A1 | 10/2021 |
| WO | 2022123232 A1 | 6/2022 |
| WO | 2023078604 A1 | 5/2023 |
| WO | 2024194382 A1 | 9/2024 |

OTHER PUBLICATIONS

International Search Report and Written Opinion issued in Application No. PCT/IB2023/000312 on Oct. 25, 2023.
International Search Report and Written Opinion issued in Application No. PCT/US2024/055213 on Jan. 14, 2025.
Grewal et al., "Serotonin 5-HT 2A Receptor Induces TGF-β1 Expression in Mesangial Cells Via ERK: Proliferate and Fibrotic Signals," American Journal of Physiology-Renal Physiology, pp. F922-F939, Jun. 1999.
Huang et al., "Tandosirone Enhances the Anti-Myocardial Fibrosis Effect of Valsartan in Spontaneously Hypertensive Rats," Biomedicine & Pharmacotherapy 126, 10 pages (2020).
Kwon et al., "Novel 5-HT7 Receptor Antagonists Module Intestinal Immune Responses and Reduce Severity of Colitis," Am J Physical Gastrointest Physiol 327, G57-G69, May 7, 2024.
Dominguez-Soto et al., "Serotonin Drives the Acquisition of a Profibrotic and Anti-Inflammatory Gene Profile Through the 5-HT7R-PKA Signaling Axis," Scientific Reports, 7: 1476, Nov. 7, 2017.
Perim et al., "Cross-Talk Inhibition Between 5-HT2B and 5-HT7 Receptors in Phrenic Motor Facilitation Via NADPH Oxidase and PKA," Am J Physiol Regul Integr Comp Physiol 314, R709-R715, Jan. 31, 2018.
Li et al., "ProBDNF and its Receptors in Immune-Mediated Inflammatory Diseases: Novel Insights Into the Regulation of Metabolism and Mitochondria," Front. Immunol. 14:1155333, Apr. 18, 2023.
Nichols, "Psychedelics as Potent Anti-Inflammatory Therapeutics," Neuropharmacology 219: 1109232, Aug. 22, 2022.
Laabi et al., "Deciphering Psilocybin: Cytotoxicity, Anti-Inflammatory Effects, and Mechanistic Insights," International Immunopharmacology 10: 111753, Feb. 23, 2024.
Nkadimeng et al., Anti-Inflammatory Effects of Four Psilocybin-Containing Magic Mushroom Water Extracts in Vitro on 15-Lipoxygenase Activity and on Lipopolysaccharide-Induced Cyclooxygenase-2 and Inflammatory Cytokines in Human U937 Macrophage Cells, Journal of Inflammation Research 2021:14, pp. 3729-3738, Aug. 5, 2021.
McIntyre, "Seotonin 5-HT2B Receptor Agonism and Valvular Heart Disease: Implications for the Development of Psilocybin and Related Agents," Expert Opinion on Drug Safety, DOI: 10.1080/14740338. 2023.2248883, Aug. 18, 2023.
Rouaud et al., "Microdosing Psychedelics and the Risk of Cardiac Fibrosis and Valvulopathy: Comparison to Known Cardiotoxins," Journal of Psychopharmacology, vol. 38(3), pp. 217-224, 2024.
Flanagan et al., "Psychedelics and Anti-Inflammatory Activity in Animal Models," Current Topics Behavioral Neurosciences 56, pp. 229-246, 2022.
Robinson et al., "Psilocybin and Eugenol Reduce Inflammation in Human 3D EpiIntestinal Tissue," Life 2023, 13, 2345, Dec. 15, 2023.
Coelho et al., "Condensin-Dependent Localisation of Topoisomerase II to an Axial Chromosomal Structure is Required for Sister Chromatid Resolution During Mitosis," Journal of Cell Science 116, pp. 4763-4776, 2003.
Coelho et al., "Discussion of the Indexing Algorithms Within TOPAS," IUCr Commission on Powder Diffraction Newsletter 32:43-45, 2003.

*Primary Examiner* — Yong S. Chong
(74) *Attorney, Agent, or Firm* — DLA Piper LLP (US)

(57) ABSTRACT

The present disclosure provides a method of treating or ameliorating a disease or disorder in a subject in need thereof, comprising administering to the subject a composition comprising a crystalline form of psilocin and psilocybin, wherein the crystalline form is co-crystal form A of psilocin and psilocybin. The disclosure further provides methods of stimulating inducing neuroplasticity, increasing BDNF levels, and/or decreasing neuroinflammation.

18 Claims, 17 Drawing Sheets

USES OF A CO-CRYSTAL OF PSILOCYBIN AND PSILOCIN

CROSS REFERENCE TO RELATED APPLICATIONS

This application claims benefit of priority under 35 U.S.C. § 119 (e) of U.S. Provisional Application No. 63/597,415, filed on Nov. 9, 2023. The disclosure of the prior application is herein incorporated by reference in the disclosure of this application in its entirety.

FIELD OF THE INVENTION

This invention is directed to the use of a co-crystal of psilocybin and psilocin in treating various disorders such as neuropsychiatric disorders, neurological disorders, inflammatory disorders including neuroinflammatory diseases or disorders, and cancer. The psilocybin and psilocin co-crystal may further be used to induce neuroplasticity, reduce neuroinflammation, as well as increase brain-derived neurotrophic factor (BDNF) levels, all with a lowered risk of cardiac adverse events.

BACKGROUND INFORMATION

Various natural plants and fungi contain psychedelic compounds which cause changes in brain function or activity ('neuroactive' compounds) and at higher doses can also cause individuals to experience hallucinogenic or similar experiences ('psychedelic' compounds). Among the most common type of naturally occurring psychedelics is psilocybin, which has been found in over 180 species of mushroom globally. Psilocybin-containing mushrooms also have other neuroactive and psychedelic compounds, the most abundant of which is its primary metabolite, psilocin. In humans, psilocybin is metabolized in the gastrointestinal system, primarily to psilocin, which is then absorbed and causes the psychedelic effects.

These psychedelic effects are dose-dependent, occurring typically at doses of at least 20 mg, and usually include changes in visual, auditory, and cognitive experiences. These psilocybin experiences may occur because both psilocybin and psilocin are similar in structure to the neurotransmitter serotonin (5-hydroxytryptamine, 5-HT), and both bind to a variety of 5-HT receptors. The psychedelic experiences are believed to be primarily due to activity at the 5-HT2A receptor in the brain.

In contrast to psilocybin, psilocin is chemically unstable and rapidly oxidizes when exposed to air. For this reason, there have been very few clinical or research studies on the impact of psilocin given alone or in comparison to psilocybin. Pre-clinical studies which have been carried out suggest that psilocin has a faster rate of absorption and a more rapid onset of action than psilocybin. Psilocin binds to a different range of 5-HT receptors and at different concentrations than psilocybin and as such has a different range of actions.

Because of the different properties of psilocybin and psilocin, a compound which combines both psilocybin and psilocin may be expected to have unique and beneficial properties compared to either compound alone.

SUMMARY

The present disclosure provides for methods of treating a disease or disorder, a method of inducing neuroplasticity, a method of stimulating neuronal growth, a method of increasing the number of neuronal progenitor cells, a method of increasing BDNF levels, or a method of decreasing neuroinflammation in a subject in need thereof, comprising administering to the subject a crystalline form of psilocin and psilocybin:

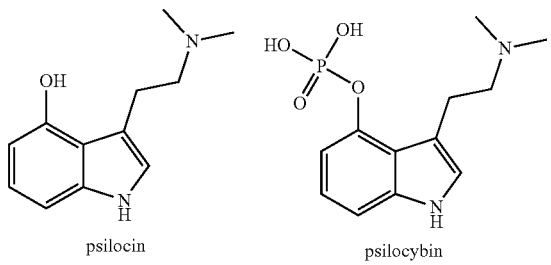

In one embodiment, the crystalline form of psilocin and psilocybin is co-crystal Form A. Co-crystal Form A may be characterized by a XRPD pattern including a significant peak at a 2θ angle of about 10.1°. A XRPD pattern of co-crystal Form A may additionally include a significant peak at 2θ angle of about 19.16°. A XRPD pattern of co-crystal Form A may additionally include significant peaks at 2θ angle of about 10.74°, about 25.3°, and about 24.07°. Yet further, a XRPD pattern of co-crystal Form A may additionally include significant peaks at 2θ angle of about 14.54°, about 16.5°, about 13.44°, about 23.42°, or about 8.62°. In one embodiment, the crystalline form is co-crystal Form A. Co-crystal Form A may be characterized by a XRPD pattern including a significant peak at a 2θ angle of about 10.1° and about 19.16°. Co-crystal Form A may be characterized by a XRPD pattern including a significant peak at a 2θ angle of about 10.1°, about 19.16°, about 14.54°, about 16.5°, about 13.44°, about 23.42°, and about 8.62°.

The present disclosure also provides for methods of treating a disease or disorder, a method of increasing the number of neuronal progenitor cells, a method of increasing BDNF levels, or a method of decreasing neuroinflammation in a subject in need thereof, comprising administering to the subject a crystalline form of psilocin and psilocybin:

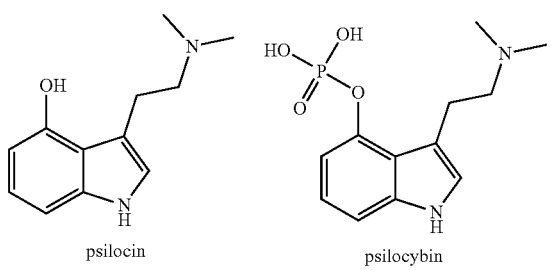

wherein the crystalline form is co-crystal Form A; and wherein Form A is characterized by a XRPD pattern comprising a significant peak at a 2θ angle of about 10.1° and about 19.16°.

In one embodiment, the disease or disorder is selected from a neuropsychiatric disease or disorder, a neurological disease or disorder, an inflammatory disease or disorder, or a cancer, disorder. In one embodiment, the inflammatory disease or disorder is a neuroinflammatory disease or disorder.

In one embodiment, the neuropsychiatric disease or disorder is addiction, developmental conditions, eating disorders, mood/affective disorders, neurotic disorders, psychosis, and sleep disorders, or a combination thereof.

In some embodiments, the neuropsychiatric disease or disorder is attention deficit hyperactivity disorder (ADHD), autism, fetal alcohol syndrome, tic disorders, bipolar disorder, depressions, mania, obsessive compulsive disorder, trichotillomania, anxiety disorders, post-traumatic stress disorder (PTSD), schizophrenia, sleep apnea, narcolepsy, insomnia, parasomnia, or a combination thereof.

In one embodiment, the neurological disease or disorder is a degenerative disease, a cognitive disease, a movement disorder, a chronic pain or headache disorder, neurodegenerative diseases, epilepsy or an epileptic seizure, or a combination thereof.

In some embodiments, the neurological disease or disorder is Agraphia, Agnosia, Alzheimer's disease, Amnesia, Amyotrophic lateral sclerosis, Aneurysm, Anosognosia, Aphasia, Apraxia, Asomatognosia, Asperger syndrome, Ataxia, Attention deficit hyperactivity disorder, Auditory processing disorder, Autism spectrum disorder, Back pain, Bell's palsy, Bipolar disorder, Brain damage, Brachial plexus injury, Brain injury, Brain tumor, Canavan disease, Capgras delusion, Carpal tunnel syndrome, Causalgia, Central pain syndrome, Central pontine myelinolysis, Centronuclear myopathy, Cephalic disorder, Cerebral arteriosclerosis, Cerebral atrophy, Cerebral vasculitis, Cervical spinal stenosis, Chorea, Chronic fatigue syndrome, Chronic inflammatory demyelinating polyneuropathy, Chronic pain, Cluster headache, Complex post-traumatic stress disorder, Complex regional pain syndrome, Compression neuropathy, Cranial arteritis, Creutzfeldt-Jakob disease, Cumulative trauma disorders, Cushing's syndrome, Cyclic vomiting syndrome, Cyclothymic disorder, Dementia, Dermatillomania, Diabetic neuropathy, Diffuse sclerosis, Dysarthria, Dyscalculia, Dysphagia, Dysgraphia, Dyskinesia, Dyslexia, Dystonia, Encephalopathy, Epilepsy, Erythromelalgia, Essential tremor, Fetal alcohol syndrome, Febrile seizures, Fibromyalgia, Friedreich's ataxia, Frontotemporal dementia, Functional neurological symptom disorder, Gaucher's disease, Generalized anxiety disorder, Gray matter heterotopia, Guillain-Barré syndrome, Head injury, Headache, Hemifacial spasm, Huntington's disease, Hypoalgesia, Hypoesthesia, Inflammatory myopathy, Intracranial hypertension, Korsakoff Syndrome, Lewy body dementia, Lumbar disc disease, Lupus erythematosus—neurological sequelae, Lyme disease, Menieres disease, Migraine, Mild brain injury, Multi-infarct dementia, Multiple sclerosis, Muscular dystrophy, Myasthenia gravis, Myoclonus, Myopathy, Neuralgia, Neurofibromatosis, Neuromyotonia, Neuropathy, Niemann-Pick disease, Optic neuritis, Otosclerosis, Paraplegia, Paralysis, Paresthesia, Paresis, Parkinson's disease, Paraneoplastic diseases, Periodic paralyses, Peripheral neuropathy, Phantom limb pain, Pick's disease, Polyneuropathy, Postherpetic neuralgia, Posttraumatic stress disorder, Primary lateral sclerosis, Prion diseases, Progressive hemifacial atrophy, Progressive supranuclear palsy, Prosopagnosia, Radiculopathy, Reflex neurovascular dystrophy, Repetitive stress injury, Restless legs syndrome, Rett syndrome, Reye's syndrome, Sclerosis, Seizures, Sensory processing disorder, Sjögren's syndrome, Sleep apnoea, Spasticity, Spinal cord injury, Spinal cord tumors, Spinal muscular atrophy, Spinocerebellar ataxia, Stiff-person syndrome, Stroke, Sydenham's chorea, Traumatic encephalopathy, Tardive dyskinesia, Tarsal tunnel syndrome, Temporal arteritis, Temporal lobe epilepsy, Tinnitus, Tourette syndrome, Toxic encephalopathy, Transient ischemic attack, Transverse myelitis, Traumatic brain injury, Tremor, Trichotillomania, Trigeminal neuralgia, Vestibular schwannoma, Vertigo, Wernicke's encephalopathy, Wilson's disease, or a combination thereof.

In some embodiments, the neurological disease or disorder is dementia, Alzheimer's disease, Mild Cognitive Impairment, Parkinson's disease, chronic back pain, chronic neuropathic pain, migraine headaches, Huntington's chorea, Amyotrophic lateral sclerosis, or a combination thereof.

In one embodiment, the inflammatory disease or disorder a neuroinflammatory disease or disorder. In one embodiment, the neuroinflammatory disease or disorder is multiple sclerosis, encephalitis, systemic lupus erythematosus, myelitis, neuritis, meningitis, vasculitis, myasthenia gravis, or a combination thereof.

In one embodiment, the cancer is a neurological cancer. In one embodiment the neurological cancer is meningioma, pituitary adenoma, craniopharyngioma, schwannoma, glioma, astrocytomas, oligodendrogliomas, glioblastomas, ependymal tumors, pineal tumors, pineocytomas, and pinealoblastomas. In some embodiments the neurological cancer originates as a prostate, pancreatic, biliary, colon, rectal, liver, kidney, lung, testicular, breast, ovarian, pancreatic, brain, and head and neck cancers, melanoma, sarcoma, multiple myeloma, leukemia or lymphoma and then includes the brain, or a combination thereof.

In one embodiment, increasing BDNF levels includes an increased anti-inflammatory response in the subject. In one embodiment, decreasing neuroinflammation comprises increasing BDNF levels. In one embodiment, any of the methods disclosed herein decrease the risk of cardiovascular adverse events.

DETAILED DESCRIPTION

Figure 1:
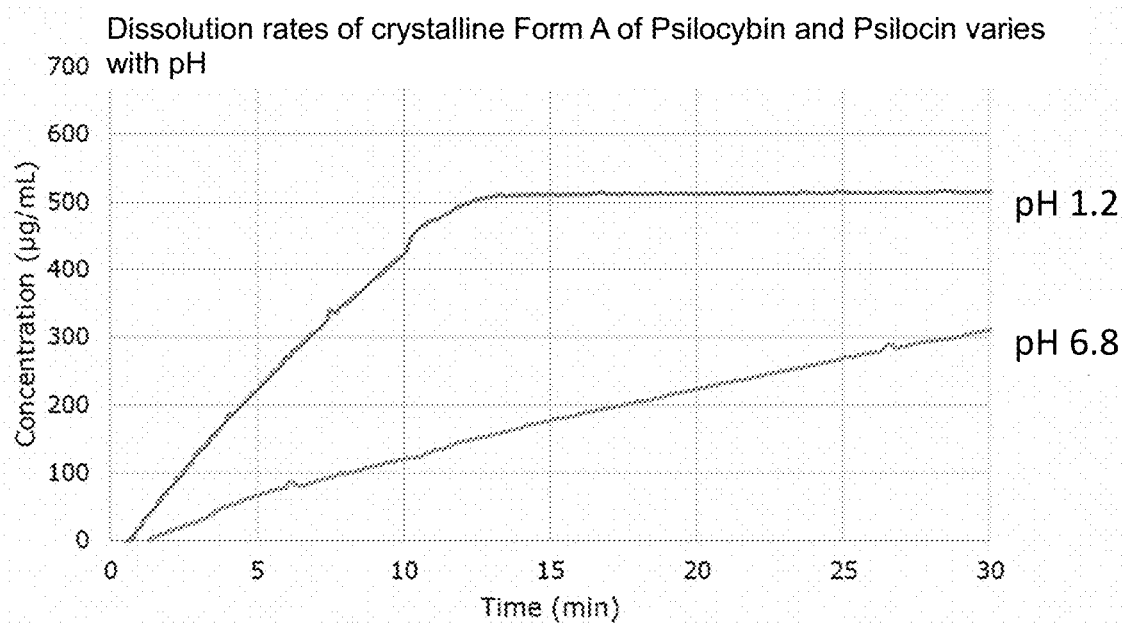
FIG. 1 shows the dissolution rates of co-crystal Form A vary with pH.

The present invention is based on the seminal discovery that co-crystals of psilocybin and psilocin may be useful for treating a disease or disorder, inducing neuroplasticity, stimulating neuronal growth, increasing the number of neuronal progenitor cells, increasing BDNF levels, or decreasing neuroinflammation in a subject in need thereof.

Before the present compositions and methods are described, it is to be understood that this invention is not limited to the particular processes, formulations, compositions, or methodologies described, as these may vary. It is also to be understood that the terminology used in the description is for the purpose of describing the particular versions or embodiments only and is not intended to limit the scope of embodiments herein which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of embodiments herein, the preferred methods, devices, and materials are now described. All publications mentioned herein are incorporated by reference in their entirety. Nothing herein is to be construed as an admission that embodiments herein are not entitled to antedate such disclosure by virtue of prior invention.

It must also be noted that as used herein and in the appended claims, the singular forms "a," "an," and "the" include plural reference unless the context clearly dictates otherwise.

The transitional term "comprising," which is synonymous with "including," "containing," or "characterized by," is inclusive or open-ended and does not exclude additional, unrecited elements or method steps.

As used herein, the term "consists of" or "consisting of" means that the composition, formulation or the method includes only the elements, steps, or ingredients specifically recited in the particular claimed embodiment or claim.

As used herein, the term "consisting essentially of" or "consists essentially of" means that the composition, formulation or the method includes only the elements, steps or ingredients specifically recited in the particular claimed embodiment or claim and may optionally include additional elements, steps or ingredients that do not materially affect the basic and novel characteristics of the particular embodiment or claim. For example, the only active ingredient(s) in the formulation or method that treats the specified condition (e.g., nutrient depletion) is the specifically recited therapeutic(s) in the particular embodiment or claim.

As used herein, two embodiments are "mutually exclusive" when one is defined to be something which is different from the other.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 1° C. to 3° C.," which is intended to include 1° C., 3° C., and everything in between to any number of significant figures (e.g., 1.255° C., 2.1° C., 2.9999° C., etc.).

As used herein, the term "about" means plus or minus 10% of the numerical value of the number with which it is being used. Therefore, about 50% means in the range of 45% to 55%. For example, "about 100° C." means a temperature in the range of 90° C. to 110° C. For example, "a 2θ angle of about 10°" means a 2θ angle in the range of 9° to 11°.

The term "substantially free" or as used herein, alone or in combination, and is used interchangeably with, the term "substantially pure", refers to a compound which is free from all other compounds within the limits of detection as measured by any means including nuclear magnetic resonance (NMR), gas chromatography/mass spectroscopy (GC/MS), or liquid chromatography/mass spectroscopy (LC/MS). In embodiments, substantially free may be less than about 1.0%, less than about 0.5%, less than about 0.4%, less than about 0.3%, less than about 0.2%, less than about 0.1%, less than about 0.05%, or less than about 0.01%.

Method of Treatment

In one embodiment, the present invention provides a method of treating a disease or disorder in a subject in need thereof, comprising administering to the subject a crystalline form of psilocin and psilocybin.

In one embodiment, the present invention provides a method of treating a disease or disorder in a subject in need thereof, comprising administering to the subject a crystalline form of psilocin and psilocybin; wherein the crystalline form of psilocin and psilocybin is co-crystal Form A.

In one embodiment, co-crystal Form A is characterized by a XRPD pattern comprising a significant peak at a 2θ angle of about 10.1° and about 19.16°. In one embodiment, the crystalline form of psilocin and psilocybin is co-crystal Form A. Co-crystal Form A may be characterized by a XRPD pattern including a significant peak at a 2θ angle of about 10.1°. A XRPD pattern of co-crystal Form A may additionally include a significant peak at 2θ angle of about 19.16°. A XRPD pattern of co-crystal Form A may additionally include significant peaks at 2θ angle of about 10.74°, about 25.3°, and about 24.07°. Yet further, a XRPD pattern of co-crystal Form A may additionally include significant peaks at 2θ angle of about 14.54°, about 16.5°, about 13.44°, about 23.42°, or about 8.62°. In one embodiment, the crystalline form is co-crystal Form A. Co-crystal Form A may be characterized by a XRPD pattern including a significant peak at a 2θ angle of about 10.1° and about 19.16°. Co-crystal Form A may be characterized by a XRPD pattern including a significant peak at a 2θ angle of about 10.1°, about 19.16°, about 14.54°, about 16.5°, about 13.44°, about 23.42°, and about 8.62°.

In one embodiment, the present invention provides a method of treating a disease or disorder in a subject in need thereof, comprising administering to the subject a crystalline form of psilocin and psilocybin; wherein the crystalline form of psilocin and psilocybin is co-crystal Form A, wherein the co-crystal Form A is characterized by a XRPD pattern comprising a significant peak at a 2θ angle of about 10.1° and about 19.16°.

In one embodiment, the present invention provides a method of treating a disease or disorder in a subject in need thereof, comprising administering to the subject a crystalline form of psilocin and psilocybin; wherein the crystalline form of psilocin and psilocybin is co-crystal Form A, wherein the co-crystal Form A is characterized by a XRPD pattern comprising a significant peak at a 2θ angle of about 10.1°, about 19.16°, about 14.54°, about 16.5°, about 13.44°, about 23.42°, and about 8.62°.

The terms "treat," "treated," "treating", or "treatment" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total, whether induction of or maintenance of), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease and prolonging disease-free survival as compared to disease-free survival if not receiving treatment and prolonging disease-free survival as compared to disease-free survival if not receiving treatment.

The term "treatment" is used interchangeably herein with the term "therapeutic method" and refers to both 1) therapeutic treatments or measures that cure, slow down, lessen symptoms of, and/or halt progression of a diagnosed pathologic conditions or disorder, and 2) and prophylactic/preventative measures. Those in need of treatment may include individuals already having a particular medical disorder as well as those who may ultimately acquire the disorder (i.e., those needing preventive measures).

The terms "therapeutically effective amount", "effective dose," "therapeutically effective dose", "effective amount," or the like refer to that amount of the subject compound that will elicit the biological or medical response of a tissue, system, animal or human that is being sought by the researcher, veterinarian, medical doctor or other clinician. Generally, the response is either amelioration of symptoms in a patient or a desired biological outcome (e.g., amelioration of symptoms of neuroinflammation). The effective amount can be determined as described herein.

The terms "administration of" and or "administering" should be understood to mean providing a pharmaceutical composition in a therapeutically effective amount to the subject in need of treatment. Administration routes can be enteral, topical or parenteral. As such, administration routes include but are not limited to intracutaneous, subcutaneous, intravenous, intraarterial, intraorbital, intracardiac, intradermal, intraperitoneal, transdermal, subarachnoid, intraspinal, oral, sublingual, buccal, rectal, nasal administrations, as well infusion. Suitable unit dosage forms, include, but are not limited to powders, tablets, pills, capsules, lozenges, suppositories, patches, nasal sprays, injectables, implantable sustained-release formulations, lipid complexes, etc.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

In some embodiments, the disease or disorder is a neuropsychiatric disease or disorder, a neurological disease or disorder, an inflammatory disease or disorder, or a cancer.

In some embodiments, the neuropsychiatric disease or disorder is addiction, developmental conditions, eating disorders, mood/affect disorders, neurotic disorders, psychosis, and sleep disorders, or a combination thereof.

In some embodiments, the neuropsychiatric disease or disorder is attention deficit hyperactivity disorder (ADHD), autism, fetal alcohol syndrome, tic disorders, bipolar disorder, depressions, mania, obsessive compulsive disorder, trichotillomania, anxiety disorders, post-traumatic stress disorder (PTSD), schizophrenia, sleep apnea, narcolepsy, insomnia, parasomnia, or a combination thereof.

In some embodiments, the disease or disorder is a neurological or disease or disorder. In some embodiments, the neurological disease or disorder is a degenerative disease, a cognitive disease, a movement disorder, a chronic pain or headache disorder, neurodegenerative diseases, epilepsy or an epileptic seizure, or a combination thereof.

In some embodiments, the neurological disease or disorder is dementia, Alzheimer's disease, Mild Cognitive Impairment, Parkinson's disease, chronic back pain, chronic neuropathic pain, migraine headaches, Huntington's chorea, Amyotrophic lateral sclerosis, or a combination thereof.

In some embodiments, the neurological disease or disorder is epilepsy or an eplileptic seizure. The terms "epilepsy" and "epileptic seizure" are used interchangeable and refer to a neurological disorder in which nerve cell activity in the brain is disturbed. An epileptic seizure is the clinical manifestation of an abnormal, excessive, and synchronized electrical discharge in the neurons. Epileptic seizures can vary from brief and nearly undetectable periods to long periods of vigorous shaking due to abnormal electrical activity in the brain. During a seizure, a person experiences abnormal behavior, symptoms, and sensations, sometimes including loss of consciousness.

In some embodiments the epileptic seizure is a tonic seizure, simple partial seizure, temporal lobe seizure, febrile seizure, grand mal seizure, absence seizure, atonic seizure, focal impaired awareness seizure, frontal lobe seizure, tonic-clonic seizure, generalized seizure, focal seizure, gelastic seizure, or a combination thereof.

In some embodiments, the disease or disorder is an inflammatory disease or disorder. In some embodiments, the inflammatory disease or disorder is a neuroinflammatory disease or disorder. Neuroinflammatory diseases and disorders occur in response to an injury or illness triggering an immune reaction. Neuroinflammatory diseases or disorders are characterized by excessive neuroinflammation that may be sustained over an extended period of time. A neuroinflammatory disease or disorder are conditions involving neuroinflammation of the nervous system, including the brain, spinal cord and neurons. Neuroinflammatory diseases or disorders are characterized by the gradual damage and loss of neurons due to neuroinflammation.

In some embodiments, the neuroinflammatory disease or disorder is multiple sclerosis, encephalitis, systemic lupus erythematosus, myelitis, neuritis, meningitis, vasculitis, myasthenia gravis, or a combination thereof. In some embodiments, the neuroinflammatory disease or disorder is rheumatoid arthritis, chronic obstructive pulmonary disease (COPD), systemic lupus erythematosus, gout, psoriatic arthritis, myositis, scleroderma, juvenile scleroderma, rheumatoid arthritis, vasculitis, ankylosing spondylitis, periodontitis, ulcerative colitis, Crohn's disease, sinusitis, asthma, Sjogren's syndrome, uveitis, or a combination thereof.

In some embodiments, the disease or disorder is a cancer. The terms "cancer" and "malignancies" refer to a group diseases characterized by abnormal and uncontrolled cell proliferation starting at one site (primary site) with the potential to invade and to spread to others sites (secondary sites, metastases) which differentiate neurological cancer (malignant tumor) from benign tumor. Virtually all the organs can be affected, leading to more than 50 types of neurological cancer that can affect humans. cancers or malignancies can result from many causes including genetic predisposition, viral infection, exposure to ionizing radiation, exposure environmental pollutant, tobacco and or alcohol use, obesity, poor diet, lack of physical activity or any combination thereof. As used herein, "neoplasm" or "tumor" including grammatical variations thereof, means new and abnormal growth of tissue, which may be benign or malignant. In a related aspect, the neoplasm is indicative of a neoplastic disease or disorder, including but not limited, to various neurological cancers.

In some embodiments, the cancer is a neurological cancer.

In some embodiments, the neurological cancer is a meningioma, pituitary adenoma, craniopharyngioma, schwannoma, glioma, astrocytomas, oligodendrogliomas, glioblastomas, ependymal tumors, pineal tumors, pineocytomas, and pinealoblastomas. In some embodiments the neurological cancer originates as a prostate, pancreatic, biliary, colon, rectal, liver, kidney, lung, testicular, breast, ovarian, pancreatic, brain, and head and neck cancers, melanoma, sarcoma, multiple myeloma, leukemia or lymphoma and then includes the brain, or a combination thereof.

In some embodiments, the method of treating the disease or disorder further comprises an increase in one or more of neuroplasticity, calcium flux, 5-HT2A receptor activity, 5-HT1A receptor activity, 5-HT7 receptor activity, TrkB expression or activity, BDNF expression or activity, or combinations thereof in the subject.

In some embodiments of the method of treating the disease or disorder includes decreased expression of a neuroinflammatory cytokine biomarker including one or more or Eotaxin, G-CSF, GM-CSF, IFNγ, IL-1α, IL-1β, IL-2, IL-3, IL-4, IL-5, IL-6, IL-7, IL-9, IL-10, IL-12p40, IL-12p70, IL-13, IL-15, IL-17, IP-10, KC, LIF, LIX, M-CSF, MCP-1, MIG, MIP-1α, MIP-1β, MIP-2, RANTES, TNFα, VEGF, or a combination thereof.

In some embodiments, the neuroinflammatory cytokine biomarker is Eotaxin.

In some embodiments, the neuroinflammatory cytokine biomarker is G-CSF.

In some embodiments, the neuroinflammatory cytokine biomarker is GM-CSF.

In some embodiments, the neuroinflammatory cytokine biomarker is IFNγ.

In some embodiments, the neuroinflammatory cytokine biomarker is IL-1α.

In some embodiments, the neuroinflammatory cytokine biomarker is IL-1β.

In some embodiments, the neuroinflammatory cytokine biomarker is IL-2.

In some embodiments, the neuroinflammatory cytokine biomarker is IL-3.

In some embodiments, the neuroinflammatory cytokine biomarker is IL-4.

In some embodiments, the neuroinflammatory cytokine biomarker is IL-5.

In some embodiments, the neuroinflammatory cytokine biomarker is IL-6.

In some embodiments, the neuroinflammatory cytokine biomarker is IL-7.

In some embodiments, the neuroinflammatory cytokine biomarker is IL-9.

In some embodiments, the neuroinflammatory cytokine biomarker is IL-10.

In some embodiments, the neuroinflammatory cytokine biomarker is IL-12p40.

In some embodiments, the neuroinflammatory cytokine biomarker is IL-12p70.

In some embodiments, the neuroinflammatory cytokine biomarker is IL-13.

In some embodiments, the neuroinflammatory cytokine biomarker is IL-15.

In some embodiments, the neuroinflammatory cytokine biomarker is Il-17.

In some embodiments, the neuroinflammatory cytokine biomarker is IP-10.

In some embodiments, the neuroinflammatory cytokine biomarker is KC.

In some embodiments, the neuroinflammatory cytokine biomarker is LIF.

In some embodiments, the neuroinflammatory cytokine biomarker is LIX.

In some embodiments, the neuroinflammatory cytokine biomarker is M-CSF.

In some embodiments, the neuroinflammatory cytokine biomarker is MCP-1.

In some embodiments, the neuroinflammatory cytokine biomarker is MIG.

In some embodiments, the neuroinflammatory cytokine biomarker is MIP-1α.

In some embodiments, the neuroinflammatory cytokine biomarker is MIP-1β.

In some embodiments, the neuroinflammatory cytokine biomarker is MIP-2.

In some embodiments, the neuroinflammatory cytokine biomarker is RANTES.

In some embodiments, the neuroinflammatory cytokine biomarker is TNFα.

In some embodiments, the neuroinflammatory cytokine biomarker is VEGF.

In another embodiment, the present invention provides a method of inducing neuroplasticity in a subject in need thereof, comprising administering to the subject a crystalline form of psilocin and psilocybin.

Neuroplasticity is a process that involves adaptive structural and functional changes to the brain. It is the ability of the nervous system to change its activity in response to intrinsic or extrinsic stimuli by reorganizing its structure, functions, or connections. Neuroplasticity includes changes in strength of mature synaptic connections, as well as the formation and elimination of synapses in adult and developing brains. Neuroplasticity is evaluated by a variety of functional and morphological endpoint measures ranging from molecular/cellular indices to changes in synaptic transmission to neurochemical alterations to changes in dendritic architecture and spine density. Examples of techniques commonly used in neuroplasticity studies are electroencephalography (EEG)/evoked potentials (ERPs), structural and functional magnetic resonance imaging (MRI) and transcranial magnetic stimulation (TMS).

In another embodiment, the present invention provides a method of stimulating neuronal growth in a subject in need thereof, comprising administering to the subject a crystalline form of psilocin and psilocybin.

In one embodiment, the crystalline form of psilocin and psilocybin is co-crystal Form A. Co-crystal Form A may be characterized by a XRPD pattern including a significant peak at a 2θ angle of about 10.1°. A XRPD pattern of co-crystal Form A may additionally include a significant peak at 2θ angle of about 19.16°. A XRPD pattern of co-crystal Form A may additionally include significant peaks at 2θ angle of about 10.74°, about 25.3°, and about 24.07°. Yet further, a XRPD pattern of co-crystal Form A may additionally include significant peaks at 2θ angle of about 14.54°, about 16.5°, about 13.44°, about 23.42°, or about 8.62°. In one embodiment, the crystalline form is co-crystal Form A. Co-crystal Form A may be characterized by a XRPD pattern including a significant peak at a 2θ angle of about 10.1° and about 19.16°. Co-crystal Form A may be characterized by a XRPD pattern including a significant peak at a 2θ angle of about 10.1°, about 19.16°, about 14.54°, about 16.5°, about 13.44°, about 23.42°, and about 8.62°.

In another embodiment, the present invention provides a method of stimulating neuronal growth in a subject in need thereof, comprising administering to the subject a crystalline form of psilocin and psilocybin, wherein the crystalline form is co-crystal Form A, wherein the co-crystal Form A is characterized by a XRPD pattern comprising a significant peak at a 2θ angle of about 10.1° and about 19.16°.

In another embodiment, the present invention provides a method of stimulating neuronal growth in a subject in need thereof, comprising administering to the subject a crystalline form of psilocin and psilocybin, wherein the crystalline form is co-crystal Form A, wherein the co-crystal Form A is characterized by a XRPD pattern comprising a significant peak at a 2θ angle of about 10.1°, about 19.16°, about 14.54°, about 16.5°, about 13.44°, about 23.42°, and about 8.62°.

In some embodiments, stimulating neuronal growth results in an increase of neurite length of about 100 μM to about 300 μM, about 110 μM to about 300 μM, about 120 μM to about 300 μM, about 130 μM to about 300 μM, about 140 μM to about 300 μM, about 150 μM to about 300 μM, about 160 μM to about 300 μM, about 170 μM to about 300 μM, about 180 μM to about 300 M, about 190 μM to about 300 M, about 200 μM to about 300 μM, about 210 μM to about 300 μM, about 220 μM to about 300 μM, about 230 μM to about 300 μM, about 240 μM to about 300 μM, about 250 M to about 300 M, about 260 μM to about 300 M, about 270 μM to about 300 μM, about 280 μM to about 300 M, about 290 μM to about 300 μM, about 100 μM to about 290 μM, about 100 μM to about 280 μM, about 100 μM to about 270 μM, about 100 μM to about 260 μM, about 100 μM to about 250 μM, about 100 μM to about 240 μM, about 100 μM to about 230 μM, about 100 μM to about 220 μM, about 100 μM to about 210 μM, about 100 μM to about 200 μM, about 100 μM to about 190 μM, about 100 μM to about 180 μM, about 100 μM to about 170 μM, about 100 μM to about 160 μM, about 100 μM to about 150 μM, about 100 μM to about 140 μM, about 100 μM to about 130 μM, or about 100 μM to about 110 μM.

In some embodiments, stimulating neuronal growth results in an increase of neurite length of about 100 μM to about 300 μM.

In some embodiments, stimulating neuronal growth results in an increase of neurite length of about 100 μM, about 110 M, about 120 μM, about 130 μM, about 140 μM, about 150 μM, about 160 μM, about 170 μM, about 190 μM, about 190 μM, about 200 μM, about 210 μM, about 220 μM, about 230 μM, about 240 μM, about 250 M, about 260 μM, about 270 μM, about 290 μM, about 290 μM, about 300 μM, or a range between any two of these values.

In some embodiments, stimulating neuronal growth results in an increase of neurite length of about 20% to about 100%, about 25% to about 100%, about 30% to about 100%, about 35% to about 100%, about 40% to about 100%, about 45% to about 100%, about 50% to about 100%, about 55% to about 100%, about 60% to about 100%, about 65% to about 100%, about 70% to about 100%, about 75% to about 100%, about 80% to about 100%, about 85% to about 100%, about 90% to about 100%, about 95% to about 100%, about 20% to about 95%, about 20% to about 90%, about 20% to about 85%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, or about 20% to about 25%.

In some embodiments, stimulating neuronal growth results in an increase of neurite length of about 20% to about 100%.

In some embodiments, stimulating neuronal growth results in an increase of neurite length of about 20%, about 25%, about 30%, about 35%, about 40%, about 45%, about 50%, about 55%, about 60%, about 65%, about 70%, about 75%, about 80%, about 85%, about 90%, about 95%, about 100%, or a range between any two of these values.

In another embodiment, the present invention provides a method of increasing the number of neuronal progenitor cells in a subject in need thereof, comprising administering to the subject a crystalline form of psilocin and psilocybin.

In another embodiment, the present invention provides a method of increasing the number of neuronal progenitor cells in a subject in need thereof, comprising administering to the subject a crystalline form of psilocin and psilocybin.

In one embodiment, the crystalline form of psilocin and psilocybin is co-crystal Form A. Co-crystal Form A may be characterized by a XRPD pattern including a significant peak at a 2θ angle of about 10.1°. A XRPD pattern of co-crystal Form A may additionally include a significant peak at 2θ angle of about 19.16°. A XRPD pattern of co-crystal Form A may additionally include significant peaks at 2θ angle of about 10.74°, about 25.3°, and about 24.07°. Yet further, a XRPD pattern of co-crystal Form A may additionally include significant peaks at 2θ angle of about 14.54°, about 16.5°, about 13.44°, about 23.42°, or about 8.62°. In one embodiment, the crystalline form is co-crystal Form A. Co-crystal Form A may be characterized by a XRPD pattern including a significant peak at a 2θ angle of about 10.1° and about 19.16°. Co-crystal Form A may be characterized by a XRPD pattern including a significant peak at a 2θ angle of about 10.1°, about 19.16°, about 14.54°, about 16.5°, about 13.44°, about 23.42°, and about 8.62°.

In another embodiment, the present invention provides a method of increasing the number of neuronal progenitor cells in a subject in need thereof, comprising administering to the subject a crystalline form of psilocin and psilocybin: wherein the crystalline form is co-crystal Form A; and wherein Form A is characterized by a XRPD pattern comprising a significant peak at a 2θ angle of about 10.1° and about 19.16°.

In another embodiment, the present invention provides a method of increasing the number of neuronal progenitor cells in a subject in need thereof, comprising administering to the subject a crystalline form of psilocin and psilocybin: wherein the crystalline form is co-crystal Form A; and wherein Form A is characterized by a XRPD pattern comprising a significant peak at a 2θ angle of about 10.1°, about 19.16°, about 14.54°, about 16.5°, about 13.44°, about 23.42°, and about 8.62°.

In some embodiments, the number of neuronal progenitor cells is increased by about 0.1% to about 10%, about 0.2% to about 10%, about 0.3% to about 10%, about 0.4% to about 10%, about 0.5% to about 10%, about 0.6% to about 10%, about 0.7% to about 10%, about 0.8% to about 10%, about 0.9% to about 10%, about 1.0% to about 10%, about 1.1% to about 10%, about 1.2% to about 10%, about 1.3% to about 10%, about 1.4% to about 10%, about 1.5% to about 10%, about 1.6% to about 10%, about 1.7% to about 10%, about 1.8% to about 10%, about 1.9% to about 10%, about 2.0% to about 10%, about 2.1% to about 10%, about 2.2% to about 10%, about 2.3% to about 10%, about 2.4% to about 10%, about 2.5% to about 10%, about 2.6% to about 10%, about 2.7% to about 10%, about 2.8% to about 10%, about 2.9% to about 10%, about 3.0% to about 10%, about 3.1% to about 10%, about 3.2% to about 10%, about 3.3% to about 10%, about 3.4% to about 10%, about 3.5% to about 10%, about 3.6% to about 10%, about 3.7% to about 10%, about 3.8% to about 10%, about 3.9% to about 10%, about 4.0% to about 10%, about 4.1% to about 10%, about 4.2% to about 10%, about 4.3% to about 10%, about 4.4% to about 10%, about 4.5% to about 10%, about 4.6% to about 10%, about 4.7% to about 10%, about 4.8% to about 10%, about 4.9% to about 10%, about 5.0% to about 10%, about 5.1% to about 10%, about 5.2% to about 10%, about 5.3% to about 10%, about 5.4% to about 10%, about 5.5% to about 10%, about 5.6% to about 10%, about 5.7% to about 10%, about 5.8% to about 10%, about 5.9% to about 10%, about 6.0% to about 10%, about 6.1% to about 10%, about 6.2% to about 10%, about 6.3% to about 10%, about 6.4% to about 10%, about 6.5% to about 10%, about 6.6% to about 10%, about 6.7% to about 10%, about 6.8% to about 10%, about 6.9% to about 10%, about 7.0% to about 10%, about 7.1% to about 10%, about 7.2% to about 10%, about 7.3% to about 10%, about 7.4% to about 10%, about 7.5% to about 10%, about 7.6% to about 10%, about 7.7% to about 10%, about 7.8% to about 10%, about 7.9% to about 10%, about 8.0% to about 10%, about 8.1% to about 10%, about 8.2% to about 10%, about 8.3% to about 10%, about 8.4% to about 10%, about 8.5% to about 10%, about 8.6% to about 10%, about 8.7% to about 10%, about 8.8% to about 10%, about 8.9% to about 10%, about 9.0% to about 10%, about 9.1% to about 10%, about 9.2% to about 10%, about 9.3% to about 10%, about 9.4% to about 10%, about 9.5% to about 10%, about 9.6% to about 10%, about 9.7% to about 10%, about 9.8% to about 10%, about 9.9% to about 10%, about 0.1% to about 9.9%, about 0.1% to about 9.8%, about 0.1% to about 9.7%, about 0.1% to about 9.6%, about 0.1% to about 9.5%, about 0.1% to about 9.4%, about 0.1% to about 9.3%, about 0.1% to about 9.2%, about 0.1% to about 9.1%, about 0.1% to about 9.0%, about 0.1% to about 8.9%, about 0.1% to about 8.8%, about 0.1% to about 8.7%, about 0.1% to about 8.6%, about 0.1% to about 8.5%, about 0.1% to about 8.4%, about 0.1% to about 8.3%, about 0.1% to about 8.2%, about 0.1% to about 8.1%, about 0.1% to about 8.0%, about 0.1% to about 7.9%, about 0.1% to about 7.8%, about 0.1% to about 7.7%, about 0.1% to about 7.6%, about 0.1% to about 7.5%, about 0.1% to about 7.4%, about 0.1% to about 7.3%, about 0.1% to about 7.2%, about 0.1% to about 7.1%, about 0.1% to about 7.0%, about 0.1% to about 6.9%, about 0.1% to about 6.8%, about 0.1% to about 6.7%, about 0.1% to about 6.6%, about 0.1% to about 6.5%, about 0.1% to about 6.4%, about 0.1% to about 6.3%, about 0.1% to about 6.2%, about 0.1% to about 6.1%, about 0.1% to about 6.0%, about 0.1% to about 5.9%, about 0.1% to about 5.8%, about 0.1% to about 5.7%, about 0.1% to about 5.6%, about 0.1% to about 5.5%, about 0.1% to about 5.4%, about 0.1% to about 5.3%, about 0.1% to about 5.2%, about 0.1% to about 5.1%, about 0.1% to about 5.0%, about 0.1% to about 4.9%, about 0.1% to about 4.8%, about 0.1% to about 4.7%, about 0.1% to about 4.6%, about 0.1% to about 4.5%, about 0.1% to about 4.4%, about 0.1% to about 4.3%, about 0.1% to about 4.2%, about 0.1% to about 4.1%, about 0.1% to about 4.0%, about 0.1% to about 3.9%, about 0.1% to about 3.8%, about 0.1% to about 3.7%, about 0.1% to about 3.6%, about 0.1% to about 3.5%, about 0.1% to about 3.4%, about 0.1% to about 3.3%, about 0.1% to about 3.2%, about 0.1% to about 3.1%, about 0.1% to about 3.0%, about 0.1% to about 2.9%, about 0.1% to about 2.8%, about 0.1% to about 2.7%, about 0.1% to about 2.6%, about 0.1% to about 2.5%, about 0.1% to about 2.4%, about 0.1% to about 2.3%, about 0.1% to about 2.2%, about 0.1% to about 2.1%, about 0.1% to about 2.0%, about 0.1% to about 1.9%, about 0.1% to about 1.8%, about 0.1% to about 1.7%, about 0.1% to about 1.6%, about 0.1% to about 1.5%, about 0.1% to about 1.4%, about 0.1% to about 1.3%, about 0.1% to about 1.2%, about 0.1% to about 1.1%, about 0.1% to about 1.0%, about 0.1% to about 0.9%, about 0.1% to about 0.8%, about 0.1% to about 0.7%, about 0.1% to about 0.6%, about 0.1% to about 0.5%, about 0.1% to about 0.4%, about 0.1% to about 0.3%, or about 0.1% to about 0.2%.

In some embodiments, the number of neuronal progenitor cells is increased by about 0.1% to about 10%

In some embodiments, the number of neuronal progenitor cells is increased by about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9%, about 10.0%, or a range between any two of these values.

In another embodiment, the present invention provides a method of increasing Brain-derived neurotrophic factor (BDNF) levels in a subject in need thereof, comprising administering to the subject a crystalline form of psilocin and psilocybin.

In another embodiment, the present invention provides a method of increasing BDNF levels in a subject in need thereof, comprising administering to the subject a crystalline form of psilocin and psilocybin.

In one embodiment, the crystalline form of psilocin and psilocybin is co-crystal Form A. Co-crystal Form A may be characterized by a XRPD pattern including a significant peak at a 2θ angle of about 10.1°. A XRPD pattern of co-crystal Form A may additionally include a significant peak at 2θ angle of about 19.16°. A XRPD pattern of co-crystal Form A may additionally include significant peaks at 2θ angle of about 10.74°, about 25.3°, and about 24.07°. Yet further, a XRPD pattern of co-crystal Form A may additionally include significant peaks at 2θ angle of about 14.54°, about 16.5°, about 13.44°, about 23.42°, or about 8.62°. In one embodiment, the crystalline form is co-crystal Form A. Co-crystal Form A may be characterized by a XRPD pattern including a significant peak at a 2θ angle of about 10.1° and about 19.16°. Co-crystal Form A may be characterized by a XRPD pattern including a significant peak at a 2θ angle of about 10.1°, about 19.16°, about 14.54°, about 16.5°, about 13.44°, about 23.42°, and about 8.62°.

In another embodiment, the present invention provides a method of increasing BDNF levels in a subject in need thereof, comprising administering to the subject a crystalline form of psilocin and psilocybin: wherein the crystalline form is co-crystal Form A; and wherein Form A is characterized by a XRPD pattern comprising a significant peak at a 2θ angle of about 10.1° and about 19.16°.

In another embodiment, the present invention provides a method of increasing BDNF levels in a subject in need thereof, comprising administering to the subject a crystalline form of psilocin and psilocybin: wherein the crystalline form is co-crystal Form A; and wherein Form A is characterized by a XRPD pattern comprising a significant peak at a 2θ angle of about 10.1°, about 19.16°, about 14.54°, about 16.5°, about 13.44°, about 23.42°, and about 8.62°.

BDNF is the most prevalent growth factor in the central nervous system. It plays an important role in neuronal survival and growth, serves as a neurotransmitter modulator, and participates in neuronal plasticity (which is essential for learning and memory). The release of BDNF strengthens the neurons already present in the brain. As a result, high levels of BDNF have been linked to improving memory and mental alertness. In some embodiments, increasing BDNF levels induces an increased anti-inflammatory response in the subject. Selective BDNF inhibitors (or indirect BDNF inhibitor such as the TrKB inhibitor ANA-12) prevent BDNF induced neurite outgrowth and thus inhibits neuronal plasticity.

In some embodiments, BDNF levels are increased.

In some embodiments, BDNF levels are increased by about 5% to about 150%, about 6% to about 150%, about 7% to about 150%, about 8% to about 150%, about 9% to about 150%, about 10% to about 150%, about 11% to about 150%, about 12% to about 150%, about 13% to about 150%, about 14% to about 150%, about 15% to about 150%, about 16% to about 150%, about 17% to about 150%, about 18% to about 150%, about 19% to about 150%, about 20% to about 150%, about 21% to about 150%, about 22% to about 150%, about 23% to about 150%, about 24% to about 150%, about 25% to about 150%, about 26% to about 150%, about 27% to about 150%, about 28% to about 150%, about 29% to about 150%, about 30% to about 150%, about 31% to about 150%, about 32% to about 150%, about 33% to about 150%, about 34% to about 150%, about 35% to about 150%, about 36% to about 150%, about 37% to about 150%, about 38% to about 150%, about 39% to about 150%, about 40% to about 150%, about 41% to about 150%, about 42% to about 150%, about 43% to about 150%, about 44% to about 150%, about 45% to about 150%, about 46% to about 150%, about 47% to about 150%, about 48% to about 150%, about 49% to about 150%, about 50% to about 150%, about 51% to about 150%, about 52% to about 150%, about 53% to about 150%, about 54% to about 150%, about 55% to about 150%, about 56% to about 150%, about 57% to about 150%, about 58% to about 150%, about 59% to about 150%, about 60% to about 150%, about 61% to about 150%, about 62% to about 150%, about 63% to about 150%, about 64% to about 150%, about 65% to about 150%, about 66% to about 150%, about 67% to about 150%, about 68% to about 150%, about 69% to about 150%, about 70% to about 150%, about 71% to about 150%, about 72% to about 150%, about 73% to about 150%, about 74% to about 150%, about 75% to about 150%, about 76% to about 150%, about 77% to about 150%, about 78% to about 150%, about 79% to about 150%, about 80% to about 150%, about 81% to about 150%, about 82% to about 150%, about 83% to about 150%, about 84% to about 150%, about 85% to about 150%, about 86% to about 150%, about 87% to about 150%, about 88% to about 150%, about 89% to about 150%, about 90% to about 150%, about 91% to about 150%, about 92% to about 150%, about 93% to about 150%, about 94% to about 150%, about 95% to about 150%, about 96% to about 150%, about 97% to about 150%, about 98% to about 150%, about 99% to about 150%, about 100% to about 150%, about 101% to about 150%, about 102% to about 150%, about 103% to about 150%, about 104% to about 150%, about 105% to about 150%, about 106% to about 150%, about 107% to about 150%, about 108% to about 150%, about 109% to about 150%, about 110% to about 150%, about 111% to about 150%, about 112% to about 150%, about 113% to about 150%, about 114% to about 150%, about 115% to about 150%, about 116% to about 150%, about 117% to about 150%, about 118% to about 150%, about 119% to about 150%, about 120% to about 150%, about 121% to about 150%, about 122% to about 150%, about 123% to about 150%, about 124% to about 150%, about 125% to about 150%, about 126% to about 150%, about 127% to about 150%, about 128% to about 150%, about 129% to about 150%, about 130% to about 150%, about 131% to about 150%, about 132% to about 150%, about 133% to about 150%, about 134% to about 150%, about 135% to about 150%, about 136% to about 150%, about 137% to about 150%, about 138% to about 150%, about 139% to about 150%, about 140% to about 150%, about 141% to about 150%, about 142% to about 150%, about 143% to about 150%, about 144% to about 150%, about 145% to about 150%, about 146% to about 150%, about 147% to about 150%, about 148% to about 150%, about 149% to about 150%, about 5% to about 149%, about 5% to about 148%, about 5% to about 147%, about 5% to about 146%, about 5% to about 145%, about 5% to about 144%, about 5% to about 143%, about 5% to about 142%, about 5% to about 141%, about 5% to about 140%, about 5% to about 139%, about 5% to about 138%, about 5% to about 137%, about 5% to about 136%, about 5% to about 135%, about 5% to about 134%, about 5% to about 133%, about 5% to about 132%, about 5% to about 131%, about 5% to about 130%, about 5% to about 129%, about 5% to about 128%, about 5% to about 127%, about 5% to about 126%, about 5% to about 125%, about 5% to about 124%, about 5% to about 123%, about 5% to about 122%, about 5% to about 121%, about 5% to about 120%, about 5% to about 119%, about 5% to about 118%, about 5% to about 117%, about 5% to about 116%, about 5% to about 115%, about 5% to about 114%, about 5% to about 113%, about 5% to about 112%, about 5% to about 111%, about 5% to about 110%, about 5% to about 109%, about 5% to about 108%, about 5% to about 107%, about 5% to about 106%, about 5% to about 105%, about 5% to about 104%, about 5% to about 103%, about 5% to about 102%, about 5% to about 101%, about 5% to about 100%, about 5% to about 99%, about 5% to about 98%, about 5% to about 97%, about 5% to about 96%, about 5% to about 95%, about 5% to about 94%, about 5% to about 93%, about 5% to about 92%, about 5% to about 91%, about 5% to about 90%, about 5% to about 89%, about 5% to about 88%, about 5% to about 87%, about 5% to about 86%, about 5% to about 85%, about 5% to about 84%, about 5% to about 83%, about 5% to about 82%, about 5% to about 81%, about 5% to about 80%, about 5% to about 79%, about 5% to about 78%, about 5% to about 77%, about 5% to about 76%, about 5% to about 75%, about 5% to about 74%, about 5% to about 73%, about 5% to about 72%, about 5% to about 71%, about 5% to about 70%, about 5% to about 69%, about 5% to about 68%, about 5% to about 67%, about 5% to about 66%, about 5% to about 65%, about 5% to about 64%, about 5% to about 63%, about 5% to about 62%, about 5% to about 61%, about 5% to about 60%, about 5% to about 59%, about 5% to about 58%, about 5% to about 57%, about 5% to about 56%, about 5% to about 55%, about 5% to about 54%, about 5% to about 53%, about 5% to about 52%, about 5% to about 51%, about 5% to about 50%, about 5% to about 49%, about 5% to about 48%, about 5% to about 47%, about 5% to about 46%, about 5% to about 45%, about 5% to about 44%, about 5% to about 43%, about 5% to about 42%, about 5% to about 41%, about 5% to about 40%, about 5% to about 39%, about 5% to about 38%, about 5% to about 37%, about 5% to about 36%, about 5% to about 35%, about 5% to about 34%, about 5% to about 33%, about 5% to about 32%, about 5% to about 31%, about 5% to about 30%, about 5% to about 29%, about 5% to about 28%, about 5% to about 27%, about 5% to about 26%, about 5% to about 25%, about 5% to about 24%, about 5% to about 23%, about 5% to about 22%, about 5% to about 21%, about 5% to about 20%, about 5% to about 19%, about 5% to about 18%, about 5% to about 17%, about 5% to about 16%, about 5% to about 15%, about 5% to about 14%, about 5% to about 13%, about 5% to about 12%, about 5% to about 11%, about 5% to about 10%, about 5% to about 9%, about 5% to about 8%, about 5% to about 7%, or about 5% to about 6%.

In some embodiments, BDNF levels are increased by about 5% to about 75%.

In some embodiments, BDNF levels are increased by about 5% to about 150%.

In some embodiments, BDNF levels are increased by about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, about 101%, about 102%, about 103%, about 104%, about 105%, about 106%, about 107%, about 108%, about 109%, about 110%, about 111%, about 112%, about 113%, about 114%, about 115%, about 116%, about 117%, about 118%, about 119%, about 120%, about 121%, about 122%, about 123%, about 124%, about 125%, about 126%, about 127%, about 128%, about 129%, about 130%, about 131%, about 132%, about 133%, about 134%, about 135%, about 136%, about 137%, about 138%, about 139%, about 140%, about 141%, about 142%, about 143%, about 144%, about 145%, about 146%, about 147%, about 148%, about 149%, about 150%, or a range between any two of these values.

In another embodiment, the present invention provides a method of decreasing neuroinflammation in a subject in need thereof, comprising administering to the subject a crystalline form of psilocin and psilocybin.

In one embodiment, the crystalline form of psilocin and psilocybin is co-crystal Form A. Co-crystal Form A may be characterized by a XRPD pattern including a significant peak at a 2θ angle of about 10.1°. A XRPD pattern of co-crystal Form A may additionally include a significant peak at 2θ angle of about 19.16°. A XRPD pattern of co-crystal Form A may additionally include significant peaks at 2θ angle of about 10.74°, about 25.3°, and about 24.07°. Yet further, a XRPD pattern of co-crystal Form A may additionally include significant peaks at 2θ angle of about 14.54°, about 16.5°, about 13.44°, about 23.42°, or about 8.62°. In one embodiment, the crystalline form is co-crystal Form A. Co-crystal Form A may be characterized by a XRPD pattern including a significant peak at a 2θ angle of about 10.1° and about 19.16°. Co-crystal Form A may be characterized by a XRPD pattern including a significant peak at a 2θ angle of about 10.1°, about 19.16°, about 14.54°, about 16.5°, about 13.44°, about 23.42°, and about 8.62°.

In another embodiment, the present invention provides a method of decreasing neuroinflammation in a subject in need thereof, comprising administering to the subject a crystalline form of psilocin and psilocybin: wherein the crystalline form is co-crystal Form A; and wherein Form A is characterized by a XRPD pattern comprising a significant peak at a 2θ angle of about 10.1° and about 19.16°.

In another embodiment, the present invention provides a method of decreasing neuroinflammation in a subject in need thereof, comprising administering to the subject a crystalline form of psilocin and psilocybin: wherein the crystalline form is co-crystal Form A; and wherein Form A is characterized by a XRPD pattern comprising a significant peak at a 2θ angle of about 10.1°, about 19.16°, about 14.54°, about 16.5°, about 13.44°, about 23.42°, and about 8.62°.

Inflammation is part of the biological response of body tissues to harmful stimuli. However, left unchecked, can damage healthy cells, tissues and organs, and may cause internal scarring, tissue death and damage to the DNA in previously healthy cells can be determined by measuring expression levels of a neuroinflammatory biomarker.

In some embodiments, the anti-inflammatory response comprises a decreased expression of a neuroinflammatory biomarker. In some embodiments, the neuroinflammatory biomarker including one or more of Eotaxin, G-CSF, GM-CSF, IFNγ, IL-1α, IL-1β, IL-2, IL-3, IL-4, IL-5, IL-6, IL-7, IL-9, IL-10, IL-12p40, IL-12p70, IL-13, IL-15, IL-17, IP-10, KC, LIF, LIX, M-CSF, MCP-1, MIG, MIP-1α, MIP-1β, MIP-2, RANTES, TNFα, VEGF, or a combination thereof.

In some embodiments, the neuroinflammatory cytokine biomarker is Eotaxin.

In some embodiments, the neuroinflammatory cytokine biomarker is G-CSF.

In some embodiments, the neuroinflammatory cytokine biomarker is GM-CSF.

In some embodiments, the neuroinflammatory cytokine biomarker is IFNγ.

In some embodiments, the neuroinflammatory cytokine biomarker is IL-1α.

In some embodiments, the neuroinflammatory cytokine biomarker is IL-1β.

In some embodiments, the neuroinflammatory cytokine biomarker is IL-2.

In some embodiments, the neuroinflammatory cytokine biomarker is IL-3.

In some embodiments, the neuroinflammatory cytokine biomarker is IL-4.

In some embodiments, the neuroinflammatory cytokine biomarker is IL-5.

In some embodiments, the neuroinflammatory cytokine biomarker is IL-6.

In some embodiments, the neuroinflammatory cytokine biomarker is IL-7.

In some embodiments, the neuroinflammatory cytokine biomarker is IL-9.

In some embodiments, the neuroinflammatory cytokine biomarker is IL-10.

In some embodiments, the neuroinflammatory cytokine biomarker is IL-12p40.

In some embodiments, the neuroinflammatory cytokine biomarker is IL-12p70.

In some embodiments, the neuroinflammatory cytokine biomarker is IL-13.

In some embodiments, the neuroinflammatory cytokine biomarker is IL-15.

In some embodiments, the neuroinflammatory cytokine biomarker is Il-17.

In some embodiments, the neuroinflammatory cytokine biomarker is IP-10.

In some embodiments, the neuroinflammatory cytokine biomarker is KC.

In some embodiments, the neuroinflammatory cytokine biomarker is LIF.

In some embodiments, the neuroinflammatory cytokine biomarker is LIX.

In some embodiments, the neuroinflammatory cytokine biomarker is M-CSF.

In some embodiments, the neuroinflammatory cytokine biomarker is MCP-1.

In some embodiments, the neuroinflammatory cytokine biomarker is MIG.

In some embodiments, the neuroinflammatory cytokine biomarker is MIP-1α.

In some embodiments, the neuroinflammatory cytokine biomarker is MIP-1β.

In some embodiments, the neuroinflammatory cytokine biomarker is MIP-2.

In some embodiments, the neuroinflammatory cytokine biomarker is RANTES.

In some embodiments, the neuroinflammatory cytokine biomarker is TNFα.

In some embodiments, the neuroinflammatory cytokine biomarker is VEGF.

In some embodiments, the neuroinflammatory cytokine biomarker is decreased in expression by about 1% to about 80%, about 2% to about 80%, about 3% to about 80%, about 4% to about 80%, about 5% to about 80%, about 6% to about 80%, about 7% to about 80%, about 8% to about 80%, about 9% to about 80%, about 10% to about 80%, about 11% to about 80%, about 12% to about 80%, about 13% to about 80%, about 14% to about 80%, about 15% to about 80%, about 16% to about 80%, about 17% to about 80%, about 18% to about 80%, about 19% to about 80%, about 20% to about 80%, about 21% to about 80%, about 22% to about 80%, about 23% to about 80%, about 24% to about 80%, about 25% to about 80%, about 26% to about 80%, about 27% to about 80%, about 28% to about 80%, about 29% to about 80%, about 30% to about 80%, about 31% to about 80%, about 32% to about 80%, about 33% to about 80%, about 34% to about 80%, about 35% to about 80%, about 36% to about 80%, about 37% to about 80%, about 38% to about 80%, about 39% to about 80%, about 40% to about 80%, about 41% to about 80%, about 42% to about 80%, about 43% to about 80%, about 44% to about 80%, about 45% to about 80%, about 46% to about 80%, about 47% to about 80%, about 48% to about 80%, about 49% to about 80%, about 50% to about 80%, about 51% to about 80%, about 52% to about 80%, about 53% to about 80%, about 54% to about 80%, about 55% to about 80%, about 56% to about 80%, about 57% to about 80%, about 58% to about 80%, about 59% to about 80%, about 60% to about 80%, about 61% to about 80%, about 62% to about 80%, about 63% to about 80%, about 64% to about 80%, about 65% to about 80%, about 66% to about 80%, about 67% to about 80%, about 68% to about 80%, about 69% to about 80%, about 70% to about 80%, about 71% to about 80%, about 72% to about 80%, about 73% to about 80%, about 74% to about 80%, about 75% to about 80%, about 76% to about 80%, about 77% to about 80%, about 78% to about 80%, about 79% to about 80%, about 1% to about 79%, about 1% to about 78%, about 1% to about 77%, about 1% to about 76%, about 1% to about 75%, about 1% to about 74%, about 1% to about 73%, about 1% to about 72%, about 1% to about 71%, about 1% to about 70%, about 1% to about 69%, about 1% to about 68%, about 1% to about 67%, about 1% to about 66%, about 1% to about 65%, about 1% to about 64%, about 1% to about 63%, about 1% to about 62%, about 1% to about 61%, about 1% to about 60%, about 1% to about 59%, about 1% to about 58%, about 1% to about 57%, about 1% to about 56%, about 1% to about 55%, about 1% to about 54%, about 1% to about 53%, about 1% to about 52%, about 1% to about 51%, about 1% to about 50%, about 1% to about 49%, about 1% to about 48%, about 1% to about 47%, about 1% to about 46%, about 1% to about 45%, about 1% to about 44%, about 1% to about 43%, about 1% to about 42%, about 1% to about 41%, about 1% to about 40%, about 1% to about 39%, about 1% to about 38%, about 1% to about 37%, about 1% to about 36%, about 1% to about 35%, about 1% to about 34%, about 1% to about 33%, about 1% to about 32%, about 1% to about 31%, about 1% to about 30%, about 1% to about 29%, about 1% to about 28%, about 1% to about 27%, about 1% to about 26%, about 1% to about 25%, about 1% to about 24%, about 1% to about 23%, about 1% to about 22%, about 1% to about 21%, about 1% to about 20%, about 1% to about 19%, about 1% to about 18%, about 1% to about 17%, about 1% to about 16%, about 1% to about 15%, about 1% to about 14%, about 1% to about 13%, about 1% to about 12%, about 1% to about 11%, about 1% to about 10%, about 1% to about 9%, about 1% to about 8%, about 1% to about 7%, about 1% to about 6%, about 1% to about 5%, about 1% to about 4%, about 1% to about 3%, or about 1% to about 2%.

In some embodiments, the neuroinflammatory cytokine biomarker is decreased in expression by about 1% to about 80%.

In some embodiments, the neuroinflammatory cytokine biomarker is decreased in expression by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, or a range between any two of these values.

In some embodiments, the neuroinflammatory cytokine biomarker is decreased after acute administration or exposure to a crystalline form of psilocin and psilocybin.

As used herein, the terms "acute administration" and "acute exposure" refer to refer to a single administration.

In some embodiments, the neuroinflammatory cytokine biomarker is decreased after chronic administration to a crystalline form of psilocin and psilocybin.

As used herein, the terms "chronic administration" and "chronic exposure" refer to a repeated daily administration for a minimum of 5 days. In some embodiments the co-crystal Form A is administered for 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, or 40 days. In some embodiments the co-crystal Form A is administered for 5 days. In some embodiments the co-crystal Form A is administered for 6 days. In some embodiments the co-crystal Form A is administered for 7 days. In some embodiments the co-crystal Form A is administered for 8 days, In some embodiments the co-crystal Form A is administered for 9 days. In some embodiments the co-crystal Form A is administered for 10 days. In some embodiments the co-crystal Form A is administered for 11 days. In some embodiments the co-crystal Form A is administered for 12 days. In some embodiments the co-crystal Form A is administered for 13 days. In some embodiments the co-crystal Form A is administered for 14 days. In some embodiments the co-crystal Form A is administered for 15 days. In some embodiments the co-crystal Form A is administered for 16 days. In some embodiments the co-crystal Form A is administered for 17 days. In some embodiments the co-crystal Form A is administered for 18 days. In some embodiments the co-crystal Form A is administered for 19 days. In some embodiments the co-crystal Form A is administered for 20 days. In some embodiments the co-crystal Form A is administered for 21 days, In some embodiments the co-crystal Form A is administered for 22 days, In some embodiments the co-crystal Form A is administered for 23 days. In some embodiments the co-crystal Form A is administered for 24 days. In some embodiments the co-crystal Form A is administered for 25 days. In some embodiments the co-crystal Form A is administered for 26 days. In some embodiments the co-crystal Form A is administered for 27 days. In some embodiments the co-crystal Form A is administered for 28 days. In some embodiments the co-crystal Form A is administered for 29 days. In some embodiments the co-crystal Form A is administered for 30 days. In some embodiments the co-crystal Form A is administered for 31 days. In some embodiments the co-crystal Form A is administered for 32 days. In some embodiments the co-crystal Form A is administered for 33 days. In some embodiments the co-crystal Form A is administered for 34 days. In some embodiments the co-crystal Form A is administered for 35 days. In some embodiments the co-crystal Form A is administered for 36 days. In some embodiments the co-crystal Form A is administered for 37 days. In some embodiments the co-crystal Form A is administered for 38 days. In some embodiments the co-crystal Form A is administered for 39 days. In some embodiments the co-crystal Form A is administered for 40 days.

In some embodiments of the methods disclosed herein, the administering of the crystalline form of psilocin and psilocybin is an acute administration.

In some embodiments of the methods disclosed herein, the administering of the crystalline form of psilocin and psilocybin is a chronic administration.

In some embodiments, decreasing neuroinflammation comprises increasing BDNF levels.

In some embodiments, BDNF levels are increased by about 5% to about 150%, about 6% to about 150%, about 7% to about 150%, about 8% to about 150%, about 9% to about 150%, about 10% to about 150%, about 11% to about 150%, about 12% to about 150%, about 13% to about 150%, about 14% to about 150%, about 15% to about 150%, about 16% to about 150%, about 17% to about 150%, about 18% to about 150%, about 19% to about 150%, about 20% to about 150%, about 21% to about 150%, about 22% to about 150%, about 23% to about 150%, about 24% to about 150%, about 25% to about 150%, about 26% to about 150%, about 27% to about 150%, about 28% to about 150%, about 29% to about 150%, about 30% to about 150%, about 31% to about 150%, about 32% to about 150%, about 33% to about 150%, about 34% to about 150%, about 35% to about 150%, about 36% to about 150%, about 37% to about 150%, about 38% to about 150%, about 39% to about 150%, about 40% to about 150%, about 41% to about 150%, about 42% to about 150%, about 43% to about 150%, about 44% to about 150%, about 45% to about 150%, about 46% to about 150%, about 47% to about 150%, about 48% to about 150%, about 49% to about 150%, about 50% to about 150%, about 51% to about 150%, about 52% to about 150%, about 53% to about 150%, about 54% to about 150%, about 55% to about 150%, about 56% to about 150%, about 57% to about 150%, about 58% to about 150%, about 59% to about 150%, about 60% to about 150%, about 61% to about 150%, about 62% to about 150%, about 63% to about 150%, about 64% to about 150%, about 65% to about 150%, about 66% to about 150%, about 67% to about 150%, about 68% to about 150%, about 69% to about 150%, about 70% to about 150%, about 71% to about 150%, about 72% to about 150%, about 73% to about 150%, about 74% to about 150%, about 75% to about 150%, about 76% to about 150%, about 77% to about 150%, about 78% to about 150%, about 79% to about 150%, about 80% to about 150%, about 81% to about 150%, about 82% to about 150%, about 83% to about 150%, about 84% to about 150%, about 85% to about 150%, about 86% to about 150%, about 87% to about 150%, about 88% to about 150%, about 89% to about 150%, about 90% to about 150%, about 91% to about 150%, about 92% to about 150%, about 93% to about 150%, about 94% to about 150%, about 95% to about 150%, about 96% to about 150%, about 97% to about 150%, about 98% to about 150%, about 99% to about 150%, about 100% to about 150%, about 101% to about 150%, about 102% to about 150%, about 103% to about 150%, about 104% to about 150%, about 105% to about 150%, about 106% to about 150%, about 107% to about 150%, about 108% to about 150%, about 109% to about 150%, about 110% to about 150%, about 111% to about 150%, about 112% to about 150%, about 113% to about 150%, about 114% to about 150%, about 115% to about 150%, about 116% to about 150%, about 117% to about 150%, about 118% to about 150%, about 119% to about 150%, about 120% to about 150%, about 121% to about 150%, about 122% to about 150%, about 123% to about 150%, about 124% to about 150%, about 125% to about 150%, about 126% to about 150%, about 127% to about 150%, about 128% to about 150%, about 129% to about 150%, about 130% to about 150%, about 131% to about 150%, about 132% to about 150%, about 133% to about 150%, about 134% to about 150%, about 135% to about 150%, about 136% to about 150%, about 137% to about 150%, about 138% to about 150%, about 139% to about 150%, about 140% to about 150%, about 141% to about 150%, about 142% to about 150%, about 143% to about 150%, about 144% to about 150%, about 145% to about 150%, about 146% to about 150%, about 147% to about 150%, about 148% to about 150%, about 149% to about 150%, about 5% to about 149%, about 5% to about 148%, about 5% to about 147%, about 5% to about 146%, about 5% to about 145%, about 5% to about 144%, about 5% to about 143%, about 5% to about 142%, about 5% to about 141%, about 5% to about 140%, about 5% to about 139%, about 5% to about 138%, about 5% to about 137%, about 5% to about 136%, about 5% to about 135%, about 5% to about 134%, about 5% to about 133%, about 5% to about 132%, about 5% to about 131%, about 5% to about 130%, about 5% to about 129%, about 5% to about 128%, about 5% to about 127%, about 5% to about 126%, about 5% to about 125%, about 5% to about 124%, about 5% to about 123%, about 5% to about 122%, about 5% to about 121%, about 5% to about 120%, about 5% to about 119%, about 5% to about 118%, about 5% to about 117%, about 5% to about 116%, about 5% to about 115%, about 5% to about 114%, about 5% to about 113%, about 5% to about 112%, about 5% to about 111%, about 5% to about 110%, about 5% to about 109%, about 5% to about 108%, about 5% to about 107%, about 5% to about 106%, about 5% to about 105%, about 5% to about 104%, about 5% to about 103%, about 5% to about 102%, about 5% to about 101%, about 5% to about 100%, about 5% to about 99%, about 5% to about 98%, about 5% to about 97%, about 5% to about 96%, about 5% to about 95%, about 5% to about 94%, about 5% to about 93%, about 5% to about 92%, about 5% to about 91%, about 5% to about 90%, about 5% to about 89%, about 5% to about 88%, about 5% to about 87%, about 5% to about 86%, about 5% to about 85%, about 5% to about 84%, about 5% to about 83%, about 5% to about 82%, about 5% to about 81%, about 5% to about 80%, about 5% to about 79%, about 5% to about 78%, about 5% to about 77%, about 5% to about 76%, about 5% to about 75%, about 5% to about 74%, about 5% to about 73%, about 5% to about 72%, about 5% to about 71%, about 5% to about 70%, about 5% to about 69%, about 5% to about 68%, about 5% to about 67%, about 5% to about 66%, about 5% to about 65%, about 5% to about 64%, about 5% to about 63%, about 5% to about 62%, about 5% to about 61%, about 5% to about 60%, about 5% to about 59%, about 5% to about 58%, about 5% to about 57%, about 5% to about 56%, about 5% to about 55%, about 5% to about 54%, about 5% to about 53%, about 5% to about 52%, about 5% to about 51%, about 5% to about 50%, about 5% to about 49%, about 5% to about 48%, about 5% to about 47%, about 5% to about 46%, about 5% to about 45%, about 5% to about 44%, about 5% to about 43%, about 5% to about 42%, about 5% to about 41%, about 5% to about 40%, about 5% to about 39%, about 5% to about 38%, about 5% to about 37%, about 5% to about 36%, about 5% to about 35%, about 5% to about 34%, about 5% to about 33%, about 5% to about 32%, about 5% to about 31%, about 5% to about 30%, about 5% to about 29%, about 5% to about 28%, about 5% to about 27%, about 5% to about 26%, about 5% to about 25%, about 5% to about 24%, about 5% to about 23%, about 5% to about 22%, about 5% to about 21%, about 5% to about 20%, about 5% to about 19%, about 5% to about 18%, about 5% to about 17%, about 5% to about 16%, about 5% to about 15%, about 5% to about 14%, about 5% to about 13%, about 5% to about 12%, about 5% to about 11%, about 5% to about 10%, about 5% to about 9%, about 5% to about 8%, about 5% to about 7%, or about 5% to about 6%.

In some embodiments, BDNF levels are increased by about 5% to about 75%.

In some embodiments, BDNF levels are increased by about 5% to about 150%.

In some embodiments, BDNF levels are increased by about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, about 101%, about 102%, about 103%, about 104%, about 105%, about 106%, about 107%, about 108%, about 109%, about 110%, about 111%, about 112%, about 113%, about 114%, about 115%, about 116%, about 117%, about 118%, about 119%, about 120%, about 121%, about 122%, about 123%, about 124%, about 125%, about 126%, about 127%, about 128%, about 129%, about 130%, about 131%, about 132%, about 133%, about 134%, about 135%, about 136%, about 137%, about 138%, about 139%, about 140%, about 141%, about 142%, about 143%, about 144%, about 145%, about 146%, about 147%, about 148%, about 149%, about 150%, or a range between any two of these values.

In any of the methods disclosed herein, the methods decreases the risk of cardiovascular adverse events.

Drugs that are agonists at 5-HT2B receptors can cause cardiovascular adverse events. The components of co-crystal A may bind to 5-HT2B receptors and for this reason there is the potential for an increased risk of cardiovascular adverse events. Cardiovascular adverse events may result from administration of the Form A co-crystal. Cardiovascular adverse events include ventricular heart disease, cardiac fibrosis, stroke, myocardial infarction, cardiovascular death, heart failure, and ischemic cardiovascular events.

In some embodiments, the decreased risk of cardiovascular adverse events, including but not limited to, decreasing the risk of ventricular heart disease, cardiac fibrosis, or a combination thereof.

In some embodiments, the decreased risk of cardiovascular adverse events comprises maintaining plasma levels of TGF-$\beta$1.

Transforming growth factor beta (TGF-$\beta$) is a multifunctional cytokine belonging to the transforming growth factor superfamily that includes three different mammalian isoforms (TGF-$\beta$1, TGF-$\beta$2, and TGF-$\beta$3). TGF-$\beta$ may impact levels of acetylcholine, slow-wave sleep, muscle regeneration, bone density, red blood cell formation, lymphocytes (T and B cells), cytotoxic T Cell (CD8), Natural Killer cell activity, macrophages activity, inflammatory response, tissue growth, wound healing, new blood vessel formation (angiogenesis), local inflammation and fibrosis, extracellular matrix deposition, and cognitive function.

TGF-$\beta$ isoforms are upregulated and activated in myocardial diseases and have an important role in cardiac repair and remodeling, regulating the phenotype and function of cardiomyocytes, fibroblasts, immune cells and vascular cells. Cardiac injury triggers the generation of bioactive TGF-$\beta$ from latent stores, through mechanisms involving proteases, integrins and specialized extracellular matrix (ECM) proteins. Changes in the plasma levels of TGF-$\beta$ isoforms is often indicative of risk of cardiovascular injury and adverse effects.

In one embodiment the crystalline form is co-crystal Form A, co-crystal Form B, or co-crystal Form C.

In one embodiment the crystalline form is co-crystal Form A.

In one embodiment, co-crystal Form A is characterized by a XRPD pattern comprising a significant peak at a 2θ angle of about 10.1°; the XRPD pattern further comprises a significant peak at a 2θ angle of about 19.16°; at a 2θ angle of about 10.74°, about 25.3°, and about 24.07°; and/or the XRPD pattern further comprises a significant peak at a 2θ angle of about 14.54°, about 16.5°, about 13.44°, about 23.42°, and about 8.62°. In one embodiment, the XRPD pattern further comprises a significant peak at a 2θ angle of about 10.74°, about 25.3°, about 24.07°, about 14.54°, about 16.5°, about 13.44°, about 23.42°, or about 8.62°. In one embodiment, co-crystal Form A is characterized by a DSC plot comprising a sharp endothermic event at a temperature of about 255° C. In one embodiment, co-crystal Form A has a ratio of psilocybin to psilocin of about 1:1. In one embodiment, co-crystal Form A has a chemical purity of about 95% or greater. In some embodiments, co-crystal Form A contains not more than about 5 mol % of other solid forms. In some embodiments, co-crystal Form A of psilocin and psilocybin comprises about 95 mol % co-crystal Form A, about 2.5 mol % psilocin, and about 2.5 mol % psilocybin. In one embodiment, co-crystal Form A is a co-crystal formed between psilocin and psilocybin. In one embodiment, co-crystal Form A is a salt formed between psilocin and psilocybin.

In one embodiment, co-crystal Form A is characterized by unit cell parameters which are substantially equal to the following:

Unit Cell Dimensions:
  a=9.3674 (3) Å
  b=11.2660 (6) Å
  c=24.2741 (9) Å
  $\alpha$=90 degrees
  $\beta$=90 degrees
  $\gamma$=90 degrees
  Space group=$P2_12_12_1$
  Molecules/asymmetric unit=1

In one embodiment, the unit cell parameters were measured about 296K. In one embodiment, co-crystal Form A has a geometry of hydrogen bonds substantially as listed in Table A. In one embodiment, co-crystal Form A has atomic coordinates of non-hydrogen atoms substantially as listed in Table B. In one embodiment, co-crystal Form A has atomic coordinates of hydrogen atoms substantially as listed in Table C. In one embodiment, co-crystal Form A is a co-crystal formed between psilocin and psilocybin. In one embodiment, co-crystal Form A is a salt formed between psilocin and psilocybin.

In one embodiment the crystalline form is co-crystal Form B.

In one embodiment, co-crystal Form B is characterized by a XRPD pattern comprising a significant peak at a 2θ angle of about 18.54°; the XRPD pattern further comprises a significant peak at a 2θ angle of about 8.54°; the XRPD pattern further comprises a significant peak at a 2θ angle of about 22.78°, about 14.27°, and about 21.12° and/or the XRPD pattern further comprises a significant peak at a 2θ angle of about 14.12°, about 10.05°, about 9.94°, about 24.94°, and about 25.02°. In one embodiment, co-crystal Form B is characterized by a DSC plot comprising a broad endothermic event at a temperature of about 168.2° C. In one embodiment, co-crystal Form B has ratio of psilocybin to psilocin of about 1.3:1. In one embodiment, co-crystal Form B has ratio of psilocybin to psilocin of about 1:1. In one embodiment, co-crystal Form B has a chemical purity of about 95% or greater. In some embodiments, co-crystal Form B contains not more than about 5 mol % of other solid forms. In some embodiments, co-crystal Form B of psilocin and psilocybin comprises about 92 mol % co-crystal Form B, about 2.5 mol % psilocin, and about 2.5 mol % psilocybin. In one embodiment, co-crystal Form B is a co-crystal formed between psilocin and psilocybin. In one embodiment, co-crystal Form B is a salt formed between psilocin and psilocybin.

In one embodiment the crystalline form is co-crystal Form C.

In one embodiment, co-crystal Form C is characterized by a XRPD pattern comprising a significant peak at a 2θ angle of about 9.18°; the XRPD pattern further comprises a significant peak at a 2θ angle of about 17.95°; the XRPD pattern further comprises a significant peak at a 2θ angle of about 10.42°, about 24.22°, and about 18.38°; and/or the XRPD pattern further comprises a significant peak at a 2θ angle of about 19.82°, about 17.46°, about 14.82°, about 22.38°, and about 14.06°. In one embodiment, co-crystal Form C is characterized by a DSC plot comprising a broad endothermic event at a temperature of about 25-140° C., with a peak at 98.7° C. In one embodiment, co-crystal Form C has ratio of psilocybin to psilocin of about 1:1. In one embodiment, co-crystal Form C has a chemical purity of about 95% or greater. In some embodiments, co-crystal Form C contains not more than about 5 mol % of other solid forms. In some embodiments, co-crystal Form C of psilocin and psilocybin comprises about 95 mol % co-crystal Form C, about 2.5 mol % psilocin, and about 2.5 mol % psilocybin. In one embodiment, co-crystal Form C is a co-crystal formed between psilocin and psilocybin. In one embodiment, co-crystal Form C is a salt formed between psilocin and psilocybin.

Crystalline Forms

Crystalline form of psilocin and psilocybin are further elaborated below:

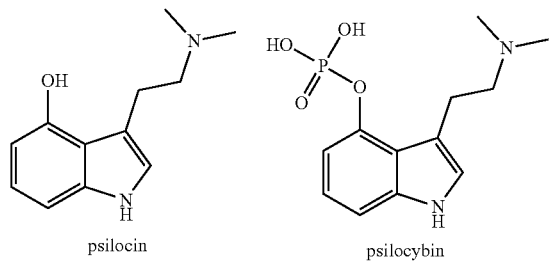

psilocin          psilocybin

Co-crystal Form A, Form B, and Form C of psilocin and psilocybin are disclosed in WO2024/003610 A1, which is hereby incorporated by reference in its entirety.

In some embodiments, the crystalline form of psilocin and psilocybin is co-crystal Form A.

In some embodiments, co-crystal Form A is characterized by a XRPD pattern comprising a significant peak at a 2θ angle of about 10.1°. In some embodiments, the XRPD pattern of co-crystal Form A may additionally comprise a significant peak at 2θ angle of about 19.16°. In some embodiments, the XRPD pattern of co-crystal Form A may additionally comprise significant peaks at 2θ angle of about 10.74°, about 25.3°, and about 24.07°. In some embodiments, the XRPD pattern of co-crystal Form A may additionally comprise significant peaks at 2θ angle of about 14.54°, about 16.5°, about 13.44°, about 23.42°, and about 8.62°. In some embodiments, the XRPD pattern further comprises a significant peak at a 2θ angle of about 10.74°, about 25.3°, about 24.07°, about 14.54°, about 16.5°, about 13.44°, about 23.42°, or about 8.62°.

In one embodiment, weight loss (1.3%) is observed between 40-200° C. by TGMS for co-crystal Form A.

In one embodiment, co-crystal Form A is characterized by a DSC plot comprising a sharp endothermic event at a temperature of about 255° C.

In some embodiments, co-crystal Form A has ratio of psilocybin to psilocin of about 1:1, about 1.1:1, about 1.2:1, about 1.3:1, about 1.4:1, about 1.5:1, about 1.6:1, about 1.7:1, about 1.8:1, about 1.9:1, about 2:1, about 1:1.1, about 1:1.2, about 1:1.3, about 1:1.4, about 1:1.5, about 1:1.6, about 1:1.7, about 1:1.8, about 1:1.9, or about 1:2. In some embodiments, co-crystal Form A has ratio of psilocybin to psilocin of about 1:1.

In some embodiments, co-crystal Form A has a chemical purity of about 95% or greater, is about 96% or greater, is about 97% or greater, is about 98% or greater, is about 98.5% or greater, is about 99% or greater, is about 99.5% or greater, or is about 99.8% or greater. In some embodiments, co-crystal Form A is substantially pure.

In some embodiments, co-crystal Form A contains not more than about 0.01 mol %, about 0.02 mol %. about 0.03 mol %, about 0.04 mol %, about 0.05 mol %, about 0.06 mol %, about 0.07 mol %, about 0.08 mol %, about 0.09 mol %, about 0.1 mol %, about 0.15 mol %, about 0.2 mol %, about 0.25 mol %, about 0.3 mol %, about 0.35 mol %, about 0.4 mol %, about 0.45 mol %, about 0.5 mol %, about 0.55 mol %, about 0.6 mol %, about 0.65 mol %, about 0.7 mol %, about 0.75 mol %, about 0.8 mol %, about 0.85 mol %, about 0.9 mol %, about 0.95 mol %, about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, about 20 mol %, of other solid forms, e.g., amorphous form. In some embodiments, co-crystal Form A of is substantially free of other solid forms.

In some embodiments, co-crystal Form A of psilocin and psilocybin comprises about 99 mol % co-crystal Form A, about 0.5 mol % psilocin, and about 0.5 mol % psilocybin; about 98 mol % co-crystal Form A, about 1.0 mol % psilocin, and about 1.0 mol % psilocybin; about 97 mol % co-crystal Form A, about 1.5 mol % psilocin, and about 1.5 mol % psilocybin; about 96 mol % co-crystal Form A, about 2.0 mol % psilocin, and about 2.0 mol % psilocybin; about 95 mol % co-crystal Form A, about 2.5 mol % psilocin, and about 2.5 mol % psilocybin; about 94 mol % co-crystal Form A, about 3.0 mol % psilocin, and about 3.0 mol % psilocybin; about 93 mol % co-crystal Form A, about 3.5 mol % psilocin, and about 3.5 mol % psilocybin; about 92 mol % co-crystal Form A, about 4.0 mol % psilocin, and about 4.0 mol % psilocybin; about 91 mol % co-crystal Form A, about 4.5 mol % psilocin, and about 4.5 mol % psilocybin; or about 90 mol % co-crystal Form A, about 5.0 mol % psilocin, and about 5.0 mol % psilocybin.

In some embodiments, co-crystal Form A is anhydrous.

In some embodiments, co-crystal Form A is a salt formed between psilocin and psilocybin.

In some embodiments, co-crystal Form A is a co-crystal formed between psilocin and psilocybin.

In some embodiments, wherein co-crystal Form A is characterized by unit cell parameters which are substantially equal to the following:

Unit Cell Dimensions:
   a=9.3674 (3) Å
   b=11.2660 (6) Å
   c=24.2741 (9) Å
   α=90 degrees
   β=90 degrees
   γ=90 degrees
   Space group=$P2_12_12_1$
   Molecules/asymmetric unit=1

In some embodiments, the unit cell parameters were measured about 296K.

In some embodiments, co-crystal Form A has a geometry of hydrogen bonds substantially as listed in Table A.

TABLE A

| D–H...A | D–H [Å] | H...A [Å] | D...A [Å] | D–H...A [°] |
|---|---|---|---|---|
| O1–H1...N23$^i$ | 0.88(2) | 1.60(2) | 2.46(2) | 162(2) |
| N11–H11...O3$^{ii}$ | 0.96(5) | 2.17(4) | 2.97(4) | 140(6) |
| N17–H17...O2$^{iii}$ | 0.85(7) | 1.83(7) | 2.59(6) | 147(8) |
| N28–H28...O1$^{iv}$ | 0.87(7) | 2.32(6) | 3.13(5) | 153(10) |
| O34–H34...O3$^v$ | 0.88(10) | 1.69(8) | 2.49(7) | 151(5) |

In some embodiments, co-crystal Form A has atomic coordinates of non-hydrogen atoms substantially as listed in Table B.

TABLE B

| | x | y | z | U(eq) |
|---|---|---|---|---|
| O1 | 0.1251(14) | 0.0326(16) | 0.4198(4) | 0.0253 |
| O2 | 0.077(3) | 0.0094(13) | 0.3153(5) | 0.0253 |
| O3 | 0.190(3) | 0.190(2) | 0.3483(6) | 0.0253 |
| P4 | 0.0916(7) | 0.0915(7) | 0.3636(3) | 0.0253 |
| O5 | −0.054(2) | 0.157(3) | 0.3724(5) | 0.0253 |
| C6 | −0.1818(8) | 0.102(5) | 0.3771(8) | 0.0253 |
| C7 | −0.221(2) | 0.009(6) | 0.4089(13) | 0.0253 |
| C8 | −0.357(3) | −0.030(9) | 0.4084(19) | 0.0253 |
| C9 | −0.466(2) | 0.022(11) | 0.375(2) | 0.0253 |
| C10 | −0.4261(9) | 0.116(10) | 0.3436(15) | 0.0253 |
| N11 | −0.512(3) | 0.188(12) | 0.3068(16) | 0.0253 |
| C12 | −0.386(5) | 0.277(10) | 0.2836(13) | 0.0253 |
| C13 | −0.265(4) | 0.250(7) | 0.3069(10) | 0.0253 |
| C14 | −0.2791(18) | 0.156(7) | 0.3445(10) | 0.0253 |
| C15 | −0.139(6) | 0.313(5) | 0.2890(13) | 0.0253 |
| C16 | −0.082(4) | 0.261(6) | 0.2343(10) | 0.0253 |
| N17 | 0.054(6) | 0.324(5) | 0.2219(15) | 0.0253 |
| C18 | 0.140(5) | 0.246(6) | 0.1809(13) | 0.0253 |
| C19 | 0.146(7) | 0.370(3) | 0.269(2) | 0.0253 |
| C21 | 0.8842(18) | 0.5884(19) | 0.9383(6) | 0.0253 |
| C22 | 0.7490(17) | 0.7295(10) | 0.9827(10) | 0.0253 |
| N23 | 0.8087(12) | 0.6116(8) | 0.9893(5) | 0.0253 |
| C24 | 0.7012(15) | 0.5244(13) | 1.0037(8) | 0.0253 |
| C25 | 0.591(2) | 0.533(3) | 0.9591(11) | 0.0253 |
| C26 | 0.508(2) | 0.422(3) | 0.9490(17) | 0.0253 |
| C27 | 0.543(5) | 0.306(3) | 0.963(2) | 0.0253 |
| N28 | 0.435(7) | 0.236(4) | 0.942(3) | 0.0253 |
| C29 | 0.337(7) | 0.302(6) | 0.917(3) | 0.0253 |
| C30 | 0.212(8) | 0.268(7) | 0.891(3) | 0.0253 |
| C31 | 0.124(7) | 0.356(9) | 0.868(3) | 0.0253 |
| C32 | 0.161(6) | 0.474(8) | 0.872(3) | 0.0253 |
| C33 | 0.292(5) | 0.508(6) | 0.899(3) | 0.0253 |
| O34 | 0.330(4) | 0.628(6) | 0.906(3) | 0.0253 |
| C35 | 0.379(5) | 0.422(5) | 0.920(2) | 0.0253 |

In some embodiments, co-crystal Form A has atomic coordinates of hydrogen atoms substantially as listed in Table C.

TABLE C

| | x | y | z | U(eq) |
|---|---|---|---|---|
| H1 | 0.1396(11) | 0.074(2) | 0.4502(3) | 0.0253 |
| H7 | −0.151(3) | −0.029(5) | 0.4319(14) | 0.0253 |
| H8 | −0.379(5) | −0.097(9) | 0.431(2) | 0.0253 |
| H9 | −0.563(3) | −0.005(13) | 0.374(2) | 0.0253 |
| H11 | −0.612(2) | 0.172(14) | 0.3030(19) | 0.0253 |
| H12 | −0.389(6) | 0.337(10) | 0.2556(15) | 0.0253 |
| H15A | −0.075(5) | 0.294(4) | 0.3185(12) | 0.0253 |
| H15B | −0.147(8) | 0.398(5) | 0.2858(18) | 0.0253 |
| H16A | −0.146(5) | 0.280(7) | 0.2048(11) | 0.0253 |
| H16B | −0.074(3) | 0.176(5) | 0.2375(8) | 0.0253 |
| H17 | 0.041(8) | 0.386(5) | 0.2026(19) | 0.0253 |
| H18A | 0.205(4) | 0.181(6) | 0.1844(12) | 0.0253 |
| H18B | 0.203(6) | 0.295(7) | 0.1601(17) | 0.0253 |
| H18C | 0.075(4) | 0.206(7) | 0.1563(10) | 0.0253 |
| H19A | 0.213(7) | 0.336(3) | 0.2941(19) | 0.0253 |
| H19B | 0.086(8) | 0.405(2) | 0.296(2) | 0.0253 |
| H19C | 0.211(9) | 0.429(4) | 0.255(2) | 0.0253 |
| H21A | 0.951(2) | 0.627(3) | 0.9141(7) | 0.0253 |
| H21B | 0.817(3) | 0.575(3) | 0.9093(5) | 0.0253 |
| H21C | 0.944(2) | 0.520(2) | 0.9427(10) | 0.0253 |
| H22A | 0.778(2) | 0.8072(10) | 0.9708(14) | 0.0253 |
| H22B | 0.715(2) | 0.7579(14) | 1.0176(12) | 0.0253 |
| H22C | 0.6710(17) | 0.7266(16) | 0.9571(11) | 0.0253 |
| H24A | 0.6599(17) | 0.542(2) | 1.0390(8) | 0.0253 |
| H24B | 0.742(2) | 0.4463(11) | 1.0054(11) | 0.0253 |
| H25A | 0.635(3) | 0.565(3) | 0.9267(9) | 0.0253 |
| H25B | 0.5179(14) | 0.587(3) | 0.9706(16) | 0.0253 |
| H27 | 0.629(5) | 0.2905(18) | 0.984(3) | 0.0253 |
| H28 | 0.436(8) | 0.159(4) | 0.946(4) | 0.0253 |
| H30 | 0.186(9) | 0.185(8) | 0.890(4) | 0.0253 |
| H31 | 0.037(8) | 0.334(10) | 0.851(4) | 0.0253 |
| H32 | 0.100(6) | 0.533(9) | 0.856(4) | 0.0253 |
| H34 | 0.294(4) | 0.682(7) | 0.884(3) | 0.0253 |

In some embodiments, the crystalline form of psilocin and psilocybin is co-crystal Form B.

In some embodiments, co-crystal Form B is characterized by a XRPD pattern comprising a significant peak at a 2θ angle of about 18.54°. In some embodiments, co-crystal Form B is characterized by a XRPD pattern of co-crystal Form B may additionally comprise a significant peak at 2θ angle of about 8.54°. In some embodiments, co-crystal Form B is characterized by a XRPD pattern of co-crystal Form B may additionally comprise significant peaks at 2θ angle of about 22.78°, about 14.27°, and about 21.12°. In some embodiments, co-crystal Form B is characterized by a XRPD pattern of co-crystal Form B may additionally comprise significant peaks at 2θ angle of about 14.12°, about 10.05°, about 9.94°, about 24.94°, and about 25.02°.

In one embodiment, weight loss (15.8%) is observed between 40-200° C. by TGMS for co-crystal Form B.

In one embodiment, co-crystal Form B is characterized by a DSC plot comprising a broad endothermic event at a temperature of about 168.2° C.

In some embodiments, co-crystal Form B has ratio of psilocybin to psilocin of about 1:1, about 1.1:1, about 1.2:1, about 1.3:1, about 1.4:1, about 1.5:1, about 1.6:1, about 1.7:1, about 1.8:1, about 1.9:1, about 2:1, about 1:1.1, about 1:1.2, about 1:1.3, about 1:1.4, about 1:1.5, about 1:1.6, about 1:1.7, about 1:1.8, about 1:1.9, or about 1:2. In some embodiments, co-crystal Form B has ratio of psilocybin to psilocin of about 1.3:1. In some embodiments, co-crystal Form B has ratio of psilocybin to psilocin of about 1:1.

In some embodiments, co-crystal Form B has a chemical purity of about 95% or greater, is about 96% or greater, is about 97% or greater, is about 98% or greater, is about 98.5% or greater, is about 99% or greater, is about 99.5% or greater, or is about 99.8% or greater. In some embodiments, co-crystal Form B is substantially pure.

In some embodiments, co-crystal Form B contains not more than about 0.01 mol %, about 0.02 mol %. about 0.03 mol %, about 0.04 mol %, about 0.05 mol %, about 0.06 mol %, about 0.07 mol %, about 0.08 mol %, about 0.09 mol %, about 0.1 mol %, about 0.15 mol %, about 0.2 mol %, about 0.25 mol %, about 0.3 mol %, about 0.35 mol %, about 0.4 mol %, about 0.45 mol %, about 0.5 mol %, about 0.55 mol %, about 0.6 mol %, about 0.65 mol %, about 0.7 mol %, about 0.75 mol %, about 0.8 mol %, about 0.85 mol %, about 0.9 mol %, about 0.95 mol %, about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, about 20 mol %, of other solid forms, e.g., amorphous form. In some embodiments, co-crystal Form B of is substantially free of other solid forms.

In some embodiments, co-crystal Form B is anhydrous.

In some embodiments, co-crystal Form B is a salt formed between psilocin and psilocybin.

In some embodiments, co-crystal Form B is a co-crystal formed between psilocin and psilocybin.

In some embodiments, the crystalline form of psilocin and psilocybin is co-crystal Form C.

In some embodiments, co-crystal Form C is characterized by a XRPD pattern comprising a significant peak at a 2θ angle of about 9.18°. In some embodiments, co-crystal Form C is characterized by a XRPD pattern of co-crystal Form C may additionally comprise a significant peak at 2θ angle of about 17.95°. In some embodiments, co-crystal Form C is characterized by a XRPD pattern of co-crystal Form C may additionally comprise significant peaks at 2θ angle of about 10.42°, about 24.22°, and about 18.38°. In some embodiments, co-crystal Form C is characterized by a XRPD pattern of co-crystal Form C may additionally comprise significant peaks at 2θ angle of about 19.82°, about 17.46°, about 14.82°, about 22.38°, and about 14.06°.

In one embodiment, weight loss (13.5%) is observed between 40-160° C. by TGMS for co-crystal Form C.

In one embodiment, co-crystal Form C is characterized by a DSC plot comprising a broad endothermic event at a temperature of about 25-140° C., with a peak at 98.7° C.

In some embodiments, co-crystal Form C has ratio of psilocybin to psilocin of about 1:1, about 1.1:1, about 1.2:1, about 1.3:1, about 1.4:1, about 1.5:1, about 1.6:1, about 1.7:1, about 1.8:1, about 1.9:1, about 2:1, about 1:1.1, about 1:1.2, about 1:1.3, about 1:1.4, about 1:1.5, about 1:1.6, about 1:1.7, about 1:1.8, about 1:1.9, or about 1:2 . . . . In some embodiments, co-crystal Form C has ratio of psilocybin to psilocin of about 1:1.

In some embodiments, co-crystal Form C has a chemical purity of about 95% or greater, is about 96% or greater, is about 97% or greater, is about 98% or greater, is about 98.5% or greater, is about 99% or greater, is about 99.5% or greater, or is about 99.8% or greater. In some embodiments, co-crystal Form C is substantially pure.

In some embodiments, co-crystal Form C contains not more than about 0.01 mol %, about 0.02 mol %. about 0.03 mol %, about 0.04 mol %, about 0.05 mol %, about 0.06 mol %, about 0.07 mol %, about 0.08 mol %, about 0.09 mol %, about 0.1 mol %, about 0.15 mol %, about 0.2 mol %, about 0.25 mol %, about 0.3 mol %, about 0.35 mol %, about 0.4 mol %, about 0.45 mol %, about 0.5 mol %, about 0.55 mol %, about 0.6 mol %, about 0.65 mol %, about 0.7 mol %, about 0.75 mol %, about 0.8 mol %, about 0.85 mol %, about 0.9 mol %, about 0.95 mol %, about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, about 20 mol %, of other solid forms, e.g., amorphous form. In some embodiments, co-crystal Form C of is substantially free of other solid forms.

In some embodiments, co-crystal Form C is anhydrous.

In some embodiments, co-crystal Form C is a salt formed between psilocin and psilocybin.

In some embodiments, co-crystal Form C is a co-crystal formed between psilocin and psilocybin.

Pharmaceutical Compositions

In one embodiment, the present application provides pharmaceutical composition comprising a crystalline form of psilocin and psilocybin and a pharmaceutically acceptable excipient.

In one embodiment the crystalline form is co-crystal Form A, co-crystal Form B or From C. In one embodiment, co-crystal Form A is characterized by a XRPD pattern comprising a significant peak at a 2θ angle of about 10.1°; the XRPD pattern further comprises a significant peak at a 2θ angle of about 19.16°; at a 2θ angle of about 10.74°, about 25.3°, and about 24.07°; and/or the XRPD pattern further comprises a significant peak at a 2θ angle of about 14.54°, about 16.5°, about 13.44°, about 23.42°, and about 8.62°. In one embodiment, the XRPD pattern further comprises a significant peak at a 2θ angle of about 10.74°, about 25.3°, about 24.07°, about 14.54°, about 16.5°, about 13.44°, about 23.42°, or about 8.62°. In one embodiment, co-crystal Form A is characterized by a DSC plot comprising a sharp endothermic event at a temperature of about 255° C. In one embodiment, co-crystal Form A has a ratio of psilocybin to psilocin of about 1:1. In one embodiment, co-crystal Form A has a chemical purity of about 95% or greater. In some embodiments, the pharmaceutical composition of co-crystal Form A contains not more than about 5 mol % of other solid forms. In some embodiments, the pharmaceutical composition of co-crystal Form A of psilocin and psilocybin comprises about 95 mol % co-crystal Form A, about 2.5 mol % psilocin, and about 2.5 mol % psilocybin. In one embodiment, co-crystal Form A is a co-crystal formed between psilocin and psilocybin. In one embodiment, co-crystal Form A is a salt formed between psilocin and psilocybin.

In one embodiment, co-crystal Form A is characterized by unit cell parameters which are substantially equal to the following:

Unit Cell Dimensions:
a=9.3674 (3) Å
b=11.2660 (6) Å
c=24.2741 (9) Å
α=90 degrees
β=90 degrees
γ=90 degrees
Space group=P2$_1$2$_1$2$_1$
Molecules/asymmetric unit=1

In one embodiment, the unit cell parameters were measured about 296K. In one embodiment, co-crystal Form A has a geometry of hydrogen bonds substantially as listed in Table A. In one embodiment, co-crystal Form A has atomic coordinates of non-hydrogen atoms substantially as listed in Table B. In one embodiment, co-crystal Form A has atomic coordinates of hydrogen atoms substantially as listed in Table C. In one embodiment, co-crystal Form A is a co-crystal formed between psilocin and psilocybin. In one embodiment, co-crystal Form A is a salt formed between psilocin and psilocybin.

In one embodiment, co-crystal Form B is characterized by a XRPD pattern comprising a significant peak at a 2θ angle of about 18.54°; the XRPD pattern further comprises a significant peak at a 2θ angle of about 8.54°; the XRPD pattern further comprises a significant peak at a 2θ angle of about 22.78°, about 14.27°, and about 21.12° and/or the XRPD pattern further comprises a significant peak at a 2θ angle of about 14.12°, about 10.05°, about 9.94°, about 24.94°, and about 25.02°. In one embodiment, co-crystal Form B is characterized by a DSC plot comprising a broad endothermic event at a temperature of about 168.2° C. In one embodiment, co-crystal Form B has ratio of psilocybin to psilocin of about 1.3:1. In one embodiment, co-crystal Form B has ratio of psilocybin to psilocin of about 1:1. In one embodiment, co-crystal Form B has a chemical purity of about 95% or greater. In some embodiments, the pharmaceutical composition of co-crystal Form B contains not more than about 5 mol % of other solid forms. In some embodiments, the pharmaceutical composition of co-crystal Form B of psilocin and psilocybin comprises about 95 mol % co-crystal Form B, about 2.5 mol % psilocin, and about 2.5 mol % psilocybin. In one embodiment, co-crystal Form B is a co-crystal formed between psilocin and psilocybin. In one embodiment, co-crystal Form B is a salt formed between psilocin and psilocybin.

In one embodiment, co-crystal Form C is characterized by a XRPD pattern comprising a significant peak at a 2θ angle of about 9.18°; the XRPD pattern further comprises a significant peak at a 2θ angle of about 17.95°; the XRPD pattern further comprises a significant peak at a 2θ angle of about 10.42°, about 24.22°, and about 18.38°; and/or the XRPD pattern further comprises a significant peak at a 2θ angle of about 19.82°, about 17.46°, about 14.82°, about 22.38°, and about 14.06°. In one embodiment, co-crystal Form C is characterized by a DSC plot comprising a broad endothermic event at a temperature of about 25-140° C., with a peak at 98.7° C. In one embodiment, co-crystal Form C has ratio of psilocybin to psilocin of about 1:1. In one embodiment, co-crystal Form C has a chemical purity of about 95% or greater. In some embodiments, the pharmaceutical composition of co-crystal Form C contains not more than about 5 mol % of other solid forms. In some embodiments, the pharmaceutical composition of co-crystal Form C of psilocin and psilocybin comprises about 95 mol % co-crystal Form C, about 2.5 mol % psilocin, and about 2.5 mol % psilocybin. In one embodiment, co-crystal Form C is a co-crystal formed between psilocin and psilocybin. In one embodiment, co-crystal Form C is a salt formed between psilocin and psilocybin.

As used herein, "pharmaceutical composition" refers to a formulation comprising an active ingredient, and optionally a pharmaceutically acceptable carrier, diluent or excipient. The term "active ingredient" can interchangeably refer to an "effective ingredient", and is meant to refer to any agent that is capable of inducing a sought-after effect upon administration. Examples of active ingredient include, but are not limited to, chemical compound, drug, therapeutic agent, small molecule, etc. In one embodiment, the active ingredient is a crystalline form of psilocybin and psilocin, such as co-crystal Form A, co-crystal Form B or co-crystal From C described herein.

The terms "excipient" and "pharmaceutically acceptable excipient" as used herein are intended to be generally synonymous, and is used interchangeably with, the terms "carrier," "pharmaceutically acceptable carrier," "diluent," "pharmaceutically acceptable diluent." By "pharmaceutically acceptable" it is meant the carrier, diluent or excipient must be compatible with the other ingredients of the formulation and not deleterious to the recipient thereof, nor to the activity of the active ingredient of the formulation. Pharmaceutically acceptable carriers, excipients or stabilizers are well known in the art, for example Remington's Pharmaceutical Sciences, 16th edition, Osol, A. Ed. (1980). Pharmaceutically acceptable carriers, excipients, or stabilizers are nontoxic to recipients at the dosages and concentrations employed, and may include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example, Zn-protein complexes); and/or non-ionic surfactants such as TWEEN™, PLURONICS™ or polyethylene glycol (PEG). Examples of carrier include, but are not limited to, liposome, nanoparticles, ointment, micelles, microsphere, microparticle, cream, emulsion, and gel. Examples of excipient include, but are not limited to, anti-adherents such as magnesium stearate, binders such as saccharides and their derivatives (sucrose, lactose, starches, cellulose, sugar alcohols and the like) protein like gelatin and synthetic polymers, lubricants such as talc and silica, and preservatives such as antioxidants, vitamin A, vitamin E, vitamin C, retinyl palmitate, selenium, cysteine, methionine, citric acid, sodium sulfate and parabens. Examples of diluent include, but are not limited to, water, alcohol, saline solution, glycol, mineral oil and dimethyl sulfoxide (DMSO).

In one embodiment, the pharmaceutically acceptable excipient is phosphate buffer; citrate buffer; ascorbic acid; methionine; octadecyldimethylbenzyl ammonium chloride; hexamethonium chloride; benzalkonium chloride; benzethonium chloride; phenol alcohol; butyl alcohol; benzyl alcohol; methyl paraben; propyl paraben; catechol; resorcinol; cyclohexanol; 3-pentanol; m-cresol; low molecular weight (less than about 10 residues) polypeptides; serum albumin; gelatin; immunoglobulins; polyvinylpyrrolidone glycine; glutamine; asparagine; histidine; arginine; lysine; monosaccharides; disaccharides; glucose; mannose; dextrins; EDTA; trehalose, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose, including eutectic solvents, eutectic-based ionic liquids, ionic liquids, sorbitol; sodium; saline; metal surfactants; non-ionic surfactants; polyethylene glycol (PEG); magnesium stearate; water; alcohol; saline solution; glycol; mineral oil, dimethyl sulfoxide (DMSO) or a combination thereof.

The active compound can be effective over a wide dosage range and can be generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLES

Example 1

Dissolution Rate of Co-Crystal

The intrinsic dissolution rate (IDR) was determined in physiologic media SGF (pH 1.2) and SIF (pH 6.8). The IDR describes the rate of dissolution normalized for the surface area. By pressing the co-crystal Form A in a passivated aluminium dye, with standardized surface area of 0.070 cm$^2$, the dissolution rate that is obtained is related to the solid form, without the effects of the particle size and/or shape (morphology) that the solid exhibits.

The IDR method that was developed for co-crystal Form A, monitored the concentration of co-crystal Form A in solution using 2 mm pathlength in the UV-range of 294-312 nm.

The IDR was determined in simulated gastric fluid (SGF) and simulated intestinal fluid (SIF) at 37° C., in triplicate. The IDR results are reported in Table 1 and the average of the three runs was calculated. A comparison of the dissolution curves in both media is shown in FIG. 1.

The intrinsic dissolution rates were determined by the slope of the linear parts of the curves. The IDR of co-crystal Form A was 1.12 (11)×104 μg/(min*cm$^2$) in SGF and 2.57 (24)×103 μg/(min*cm$^2$) in SIF. The IDR of co-crystal Form A was fast in both media and reached 0.5 mg/mL (10 mg tablet) in SGF within 15 min, while in SIF this concentration was reached after 1 h, i.e. the IDR of co-crystal Form A was about 4 times faster in SGF than in SIF.

TABLE 1

| IDR (μg/(min * cm$^2$)) | | | | |
|---|---|---|---|---|
| Medium | Run 1 | Run 2 | Run 3 | Average |
| SGF | 1.11 × 10$^4$ | 1.23 × 10$^4$ | 1.02 × 10$^4$ | 1.12(11) × 10$^4$ |
| SIF | 2.71 × 10$^3$ | 2.30 × 10$^3$ | 2.71 × 10$^3$ | 2.57(24) × 10$^3$ |

Rotating disc intrinsic dissolution determinations were performed with Pion's AuPRO.7.0 machine equipped with 6 independent glass fibre probes each connected to a diode area. Each probe was calibrated separately. Discs were prepared in a passivated aluminium dye with a mini IDR press.

Stock solutions of co-crystal Form A were prepared in SGF buffer pH 1.2 and SIF buffer pH 6.8 with a concentration of 20.0 mg/mL. The calibration lines were prepared by measuring 6 standards in SGF and SIF. Standard 0 was the buffer solution without API and for each following standard additional 50 μL of the API solution was added to 15 mL of SGF or SIF (resulting in a calibration line with concentrations between 0-328 μg/mL). The calibration curves were used for the calculation of the amount of API in solution during measurements. Moreover the calibration curves were used to select the proper path length (2 mm).

An appropriate amount (~10 mg) of material was compressed in a passivated aluminium dye (standardized surface area of 0.070 cm2) with 80 kg of pressure for 45 seconds. The dyes were placed in their Teflon S21103D_V2 holder with magnet and placed into 20 mL glass vials. The experiment was started by the gentle addition of the dissolution media. Vials were incubated at 37° C. under continuous stirring at 100 rpm up to 4 hours. The UV-signal in the region 294-312 nm (in second derivative mode) was measured at regular time intervals. Dissolution rates were calculated over the linear parts of the curves.

These data indicate that the co-crystal Form A displays rapid dissolution that varies with pH.

Example 2

Serum Levels of Co-Crystal

Animals—Adult male and female C57BL/6 mice aged 8-10 weeks were randomly assigned to receive oral gavage (p.o) of vehicle (phosphate-buffered saline), or 3 mg/kg psilocybin or Co-crystal Form A. C57BL/6 mice were treated with 3 mg/kg of each compound via oral gavage and blood was samples from either the saphenous vein (10 min, 1 h, 4 h) or during euthanasia (30 min, 3 h, 8 h). Blood was then used to quantify psilocin levels via high performance tandem mass spectroscopy as detailed below. Data were analyzed via area under the curve (AUC) to estimate $C_{max}$, in GraphPad (v. 10). n=3-12 male and female mice. Data were excluded if psilocin levels were below the lower limit of quantification (5 ng/ml) or above the upper limit of the standard curve (4000 ng/ml).

High-performance liquid chromatography tandem mass spectroscopy—Psilocin (1 mg/mL in acetonitrile) and psilocin-$D_{10}$ standard solutions (100 μg/mL in acetonitrile) were kept at −80° C. Deuterium atoms in the internal standard (IS), psilocin-$D_{10}$, were located on the amine side chain. Additional psilocin was purchased and acetonitrile was evaporated using a rotary evaporator to purify compound for subsequent use in animal experiments. To obtain drug-free plasma, after isoflurane anesthetization, a cardiac puncture was performed to collect atrial blood from C57BL/6 mice. Blood was transferred to BD Vacutainer™ Plastic Blood Collection Tubes with Lithium Heparin and centrifuged at 2,000×g for 10 min at 4° C. The supernatant (plasma) was stored at −80° C. and used for the preparation of calibration standards and quality control samples.

Calibration standards and quality control (QC) preparation: The stock solution of psilocin was prepared at a concentration of 40,000 ng/ml in water/acetonitrile (1:1 v/v) and the psilocin-$D_{10}$ stock solution was prepared at a concentration of 5,000 ng/ml in acetonitrile. All stock solutions were stored at −20° C. Working solutions for the calibration standards were made by serial dilution of the stock psilocin with water/acetonitrile (1:1 v/v) to seven standard points in a range from 5 ng/ml to 4,000 ng/mL. To create the calibration standards, 5 μL of each working solution was combined with 45 μL of drug-free mouse plasma and mixed gently to yield seven standards at concentrations of 0.5, 1, 20, 100, 300, 380, and 400 ng/mL. To each standard, 450 μL of a protein precipitation solution (acetonitrile containing 50 ng/mL psilocin-$D_{10}$) was added. Each standard was then vigorously vortexed for 30 seconds and subsequently centrifuged at 14,000 rpm at 4° C. for 10 minutes using a VWR micro 18R centrifuge. The supernatant was transferred into HPLC vial inserts (150 μL). A double blank sample was prepared by spiking a plasma sample with 5 μL of water/acetonitrile (1:1 v/v) and extracted with 450 μL of acetonitrile. Blank (zero calibrator) samples were prepared by spiking plasma samples with 5 μL of water/acetonitrile (1:1 v/v) and extracted with 450 µL of the protein precipitation solution containing IS as described above (i.e., the blank sample contained the IS). QC samples were prepared with serial dilutions of a different working solution (3600 ng/mL) applying the same procedure described above. According to the Food and Drug Administration (FDA) and European Medicines Agency (EMA) guidelines for bioanalytical method validation, the low-quality control (LQC) sample should be within 3 times the concentration of the lower limit of quantification (LLOQ); the middle quality control (MQC) sample should be in the mid-range; and the high-quality control (HQC) sample should be at least 75% of the upper limit of quantification (ULOQ). Based on these guidelines, QC concentrations were determined to be 1.5 ng/mL, 200 ng/mL, and 360 ng/ml for LQC, MQC, and HQC, respectively.

HILIC LC-MS/MS Instrumentation: Various LC columns were tested and evaluated, including hydrophilic interaction liquid chromatography (HILIC), phenyl, phenyl-hexyl, and C18. Chromatographic separation was achieved on an Agilent 1290 infinity ultra-high performance liquid chromatography (UHPLC) system. The autosampler, maintained at 4° C., was used to inject 1.7 µL of solution for separation onto an Agilent InfinityLab Poroshell 120 HILIC-Z® UHPLC column (2.1×50 mm, 1.9 µm, 100 Å) equipped with an InfinityLab Poroshell 120 HILIC guard column (1.9 µm, 120 Å, 2.1×5 mm). The column temperature was maintained at 30° C. A gradient binary mobile phase system composed of (A) 10 mM ammonium formate buffer (pH 3.0) and (B) 0.1% formic acid in acetonitrile was set to flow at 1 mL/min. The gradient program started with 90% B and remained constant for 0.1 min. The gradient changed from 90% B to 50% B over the next 0.8 min, followed by an increase to reach the initial condition (90% B) by 1.1 min. The initial composition was held constant for an additional 0.7 min for equilibration. The total run time was 1.8 min. The flow of the mobile phase was directed to the mass spectrometer between 0.2 min and 0.6 min through an integrated divert valve, in order to decrease the contamination of the ion source. A needle wash step with methanol was employed between injections. Data processing was performed on Analyst® software, version 1.7.

Following separation, column effluent was directed to the Turbospray ionization source of a quadrupole-linear ion trap (Q-LIT) instrument, namely AB Sciex 6500 API QTrap® (AB Sciex, ON, Canada). Quantification was achieved in the multiple reaction monitoring (MRM) mode using positive ionization. Table 10 shows the quantifier and qualifier ions and their respective declustering potential (DP), collision energy (CE), and cell exit potentials (CXP). The source temperature was set at 550° C., ion spray voltage (ISV) 5500 V, curtain gas (CUR) 40, nebulizer gas (GS1) 80, heater gas pressure (GS2) 40 and an entrance potential (EP) of 10 was used for all transitions. The DP, CE, and CXP were optimized for each MRM transition to ensure ion abundance and signal stability (Table 2). Dwell time for all transitions was 50 msec at unit resolution and nitrogen gas was used in all cases. Initial optimization experiments investigating the fragmentation pattern of psilocin and IS were conducted using direct infusion. A Harvard syringe pump, set at 7 µL/min, was used for the injection of psilocin (100 ng/mL) and the IS (50 ng/mL) in acetonitrile containing 0.1% formic acid.

TABLE 2

MRM transitions for psilocin and psilocin-$D_{10}$ (IS) and the optimized MS conditions.

| | Psilocin | | |
|---|---|---|---|
| | 205.1 → 58.1 (Quantifier) | 205.1 → 160.1 (Qualifier) | Psilocin-$D_{10}$ 215.1 → 66.2 |
| De-clustering potential (DP) | 36.0 | 36.0 | 31.0 |
| Collision energy (CE) | 37.0 | 27.0 | 19.0 |
| Cell exit potential (CXP) | 16.0 | 16.0 | 8.0 |

Flow injection analysis (FIA-MS/MS) was initially tested and performed using the same conditions mentioned above but without the use of an analytical column. To do that, 5 µL of each sample was injected by the autosampler directly onto a capillary line that led to the ESI ion source of the mass spectrometer. An in-line filter assured that no large contaminant particles remaining from the protein precipitation process entered the ion source.

High-resolution MS analysis: To identify the observed interference in the LC-MS/MS analysis of psilocin in mouse plasma using a C18 column, an experiment was carried out using a high-resolution mass spectrometer. A double blank sample (extracted drug-free plasma), a psilocin solution (1000 ng/mL) in methanol/water (3:1), and an extracted plasma sample spiked with psilocin (100 ng/mL) were analyzed using the following conditions. The LC-MS/MS analysis was performed using an Ultimate 3,000 UHPLC system. The LC system was coupled to a Thermo Fisher Q-Exactive® quadrupole-orbitrap instrument equipped with a heated electrospray ionization (HESI) source operated in the positive ion mode at 3000 V. The capillary temperature and the vaporizer temperature were set to 320 and 350° C., respectively. The sheath and auxiliary gases were set to 60 and 20, respectively. The scan function "Full scan/DDMS2" was used to acquire data-dependent fragmentation data (i.e., DDMS2) for the psilocin samples. The full scan analysis (m/z 50-400) used a mass resolution of 70,000 (FWHM at m/z 200), and any ion with an m/z of 205.15±0.15 detected in full scan would automatically trigger an MS/MS analysis (m/z 50-250), which used a resolution of 17,500 (FWHM at m/z 200) and a collision energy of 30.

Prior to analysis, a six-point calibration of the instrument was performed in the positive ion mode using Pierce™ LTQ Velos ESI Positive Ion Calibration Solution, which contains "Caffeine (20 µg/mL), MRFA (1 µg/mL) and Ultramark 1621 (0.001%) in an aqueous solution of acetonitrile (50%), methanol (25%) and acetic acid (1%). The search for chemical formulas corresponding to exact mass measurements was performed using ChemCalc online service.

Method validation: The method validation followed the FDA and EMA Guidelines for Bioanalytical Method Validation, including accuracy, precision, selectivity, linearity, matrix effects, recovery, repeatability, and stability.

Calibration curve, linearity, and QCs: A standard curve comprised of seven data points, ranging from 0.5 ng/mL to 400 ng/mL, was constructed by determining the best fit of peak-area ratios (i.e., peak area ratio of the analyte to internal standard) versus the analyte concentration. A linear regression analysis weighing the standard curve with $1/x^2$ was applied. The suitability of the fitted regression model to the data set was assessed by evaluating deviation of standards from the nominal concentration and evaluating the slope, intercept, and correlation coefficient (r) of the curve. Precision and accuracy were determined within the same day (intra-day) and on three consecutive days (inter-day) using six replicates (n=6) of LLOQ (0.5 ng/ml), LQC (1.5 ng/ml), MQC (200 ng/mL), and HQC (360 ng/ml). Accuracy was accepted if the mean calculated concentration was within ±15% of the nominal concentration of the QC samples, and within ±20% of the nominal value for the LLOQ samples. The precision of the LLOQ was accepted if its coefficient of variation (CV %) was less than 20% and less than 15% for each QC level. A standard with a signal to noise ratio of 3:1 was considered as the limit of detection (LOD) while the lower limit of quantitation (LLOQ) of the method was determined based on a minimum of 5 to 10× the signal to-noise ratio of 5:1 to 10:1 noise with the acceptable precision and accuracy (within ±20% of the nominal LLOQ concentration).

Matrix effects: Matrix effects were evaluated at two QC levels (LQC and HQC) by comparing the instrument response of the analyte added to the extracted mouse plasma sample (post-spike sample), to the analyte in pure solvent (acetonitrile/water 9:1). Six C57BL/6 mouse plasma samples obtained from six individual mice were used to determine the matrix effects of the analytical method. The following equation was used to calculate the matrix effect.

$$\text{Matrix Effect \%} = \frac{\text{Peak area}_{(post-spike)}}{\text{Peak area}_{(pure\ solvent)}} \times 100$$

To investigate if Phospholipids (PLs) are possibly contributing to the observed matrix effects, MRM transitions of the three most abundant interfering Phosphatidylcholines (PCs) were monitored in a double blank sample. The monitored PL transitions were m/z 496.4→m/z 184.2 for LysoPC (C16:0), m/z 760.7→m/z 184.2 for PC (C16:0/C18:1), and m/z 786.8→m/z 184.2 for PC (C18:1/C18:1).

Selectivity: The selectivity test ensured no interference of the co-eluting components of the sample matrix at the level of LLOQ as demonstrated by analyzing six different mouse plasma samples. The method was considered selective if the observed interference in the double blank samples was less than 20% of the LLOQ for the analyte and less than 5% for the IS.

Recovery: To measure extraction recovery, the instrument response of the analyte added to the extracted mouse plasma sample (post-spike sample) was compared to the response of the analyte added to the plasma sample before extraction (pre-spike sample) in 6 replicates of LQC, MQC, and HQC.

$$\text{Extraction Recovery \%} = \frac{\text{Peak area}_{(pre-spike)}}{\text{Peak area}_{(post-spike)}} \times 100$$

Carry-over: A double blank was injected after the ULOQ to determine the carryover effects related to the analyte and the IS. Carryover was deemed significant if the areas in the double blank were more than or equal to 20% for the analyte, and more than or equal to 5% of the IS for the LLOQ sample. [19,20] The following equation was used to calculate the carryover effects.

$$\text{Carryover Effect \%} = \frac{\text{Peak area of a double blank after } ULOQ}{\text{Peak area of the } LLOQ} \times 100$$

Dilution integrity: To ensure that a diluted sample will have the same accuracy and precision as an undiluted sample, dilution integrity test was performed. A spiked plasma sample at a concentration of 4,000 ng/ml was extracted and then diluted with blank to 80 ng/ml (×50 dilution). The results were considered acceptable if the calculated accuracies were between 85% and 115% of the nominal concentration and the precision was less than 15%.

Stability: The stability of the samples was evaluated under various conditions encountered during sample preparation and analysis, as well as different storage conditions. This assessment involved using HQC and LQC samples analyzed with freshly prepared calibration curves. To examine stability, four sets of QC samples (HQC, LQC; n=6 for each level) were prepared and exposed to the following conditions before extraction and analysis: (A) room temperature for 3 hours (benchtop stability), (B) 4° C. for 24 hours (autosampler stability), (C) stored at −80° C. for 2 month (storage stability), (D) subjected to 3 freeze-thaw cycles (freeze-thaw stability). In the case of the last stability study, QC samples were frozen at −80° C. for at least 24 hours, then thawed at room temperature, refrozen at −80° C. for at least 24 hours before the next freeze-thaw cycle.

To assess the stability of the processed samples after extraction (extraction stability), two sets of LQC and HQC samples were prepared (n=12 at each QC level), extracted, and transferred to HPLC vials with inserts. The first set of LQC and HQCs (n=6 at each QC level) were placed at room temperature for 3 hours before being analyzed. The second set of QCs were stored at −80° C. for 6 days before being thawed and analyzed.

For assessing the stability of the analyte working stock solution, a 2-month stock stored at −20° C. was utilized to prepare LQC and HQC samples (n=6). These samples were then analyzed against calibration curves and QCs created from fresh stock solutions. Samples were considered stable if they fell within +15% of their respective nominal concentration.

System suitability: To ensure that there is a consistent response from the samples (i.e., system suitability), a 20 ng/mL solution of psilocin in acetonitrile/water (9:1) was injected five times at the beginning of each run and the calculated coefficient of variation (CV) was determined as an indicator of the variation in response.

Application to mouse samples: The validated method was applied to analyze samples for this study. The concentration of psilocin in blood plasma was measured from samples in the numbers of mice at times as indicated in figure legends. Blood was transferred to BD Vacutainer™ Plastic Blood Collection Tubes with Lithium Heparin: Hemogard and centrifuged at 2,000×g for 10 min at 4° C. The supernatant (plasma) was stored at −80° C. before extraction and analysis. Mouse plasma samples from the pharmacokinetic study were thawed at room temperature and gently vortexed. Samples were prepared by adding 450 μL of the protein precipitation solution (acetonitrile containing 50 ng/mL psilocin-$D_{10}$) to 50 μL of plasma sample. Each sample was vortexed for 30 sec and then centrifuged at 14,000 rpm at 4° C. for 10 min. The supernatant was transferred into HPLC vial inserts (150 μL).

Figure 2:
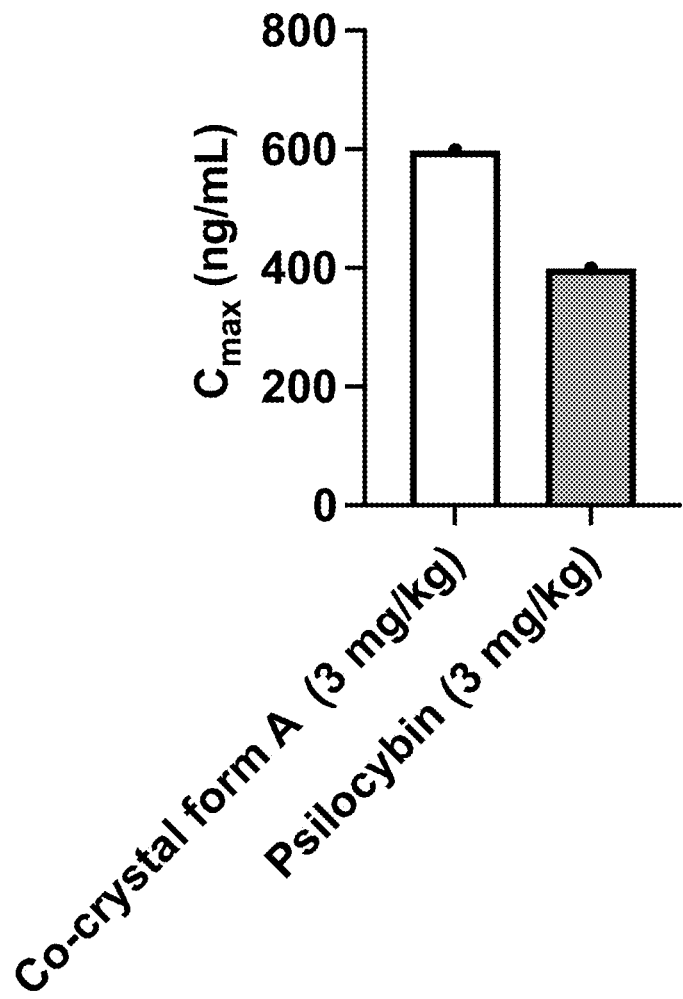
FIG. 2 shows the peak serum psilocin level ($C_{max}$) after oral administration of co-crystal Form A.
Figure 3:
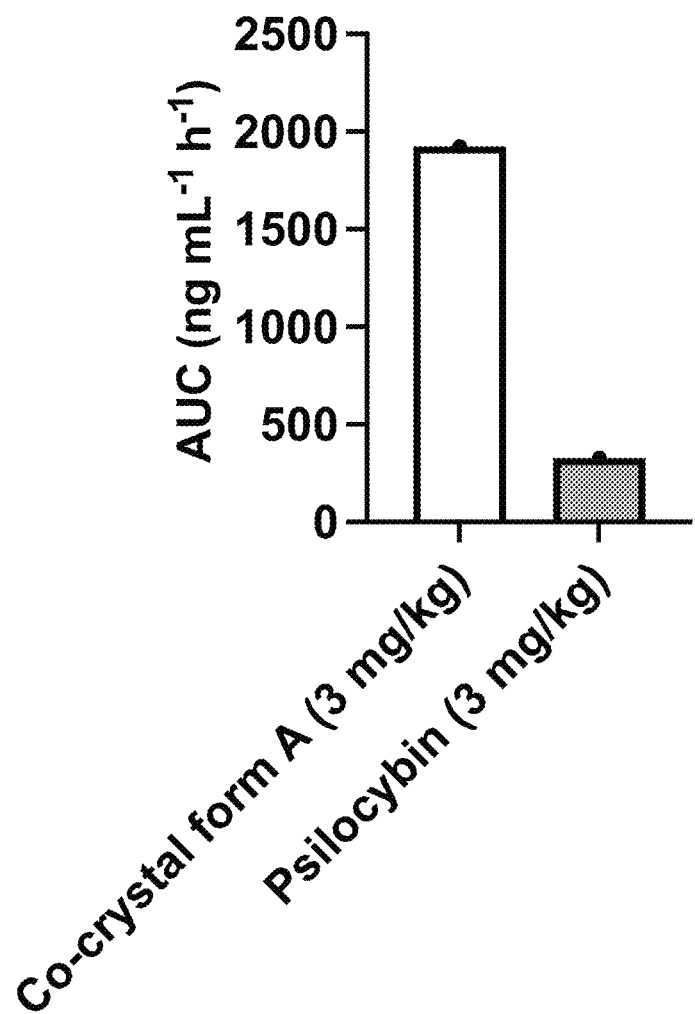
FIG. 3 shows the total serum psilocin levels after oral administration of co-crystal Form A.

Results are shown in FIGS. 2 and 3.

These data indicate that the co-crystal Form A has higher serum levels compared with psilocybin.

41

Example 3

Head Twitch Response

Animals—Adult male and female C57BL/6 mice aged 8-10 weeks were randomly assigned to receive i.p. injections of vehicle (1:1:18 ethanol:emulphor:saline), or 0.01-10 mg/kg compound.

Head-twitch response-Immediately after compound administration, mice were placed in a clear tube and monitored for 10 min to quantify head-twitch response (HTR), which was recorded as the atypical horizontal shaking of the head. Resultant dose-response curves (DRC) were fit using non-linear regression (Bell-shaped dose response, Hill Slope constrained to 1) and used to estimate efficacy and potency (GraphPad, Prism, v. 10).

Figure 4:
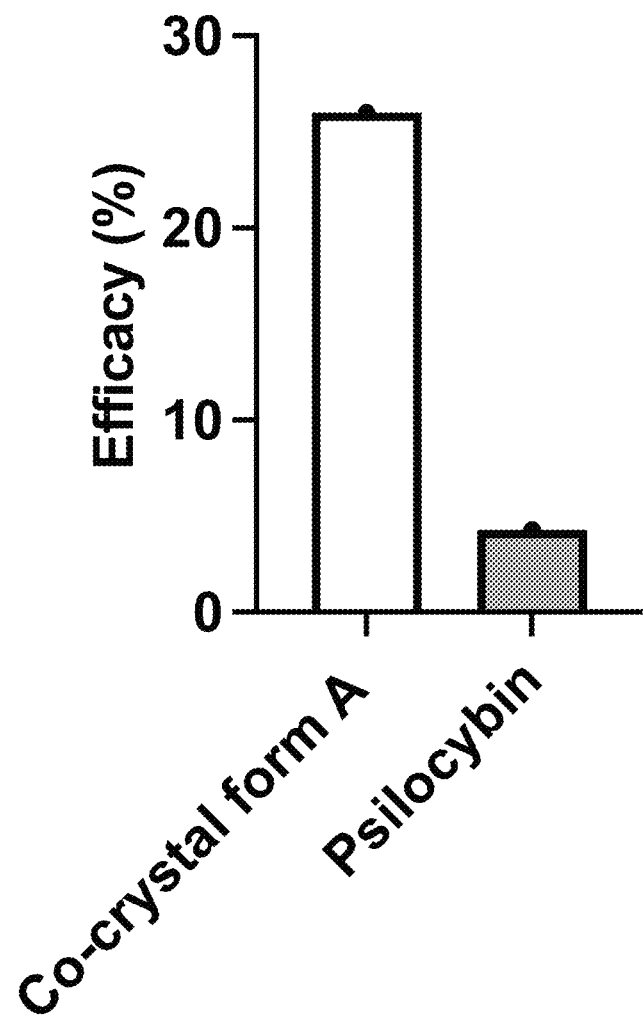
FIG. 4 shows the head twitch response efficacy 10 minutes after intraperitoneal administration co-crystal Form A.
Figure 5:
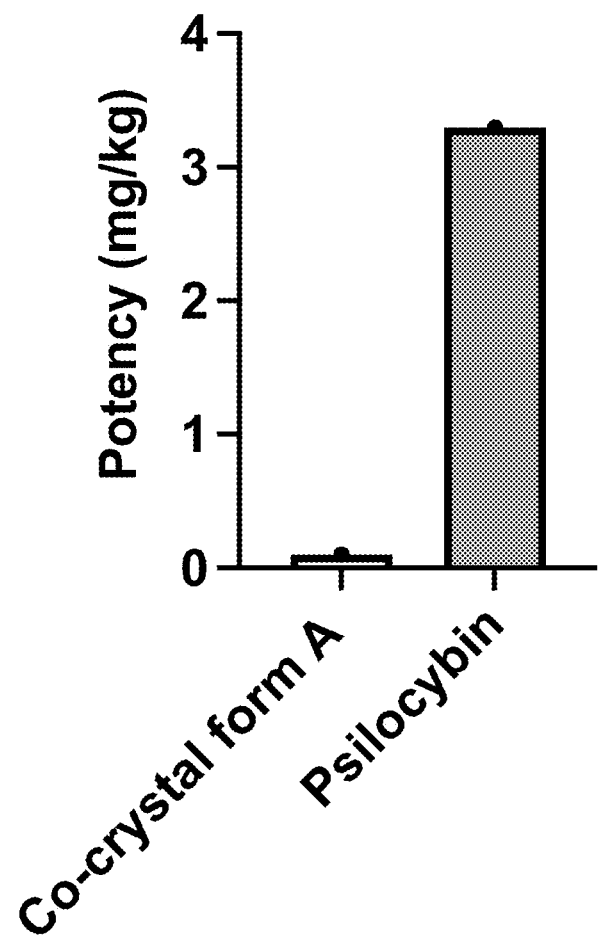
FIG. 5 shows the head twitch response potency 10 minutes after intraperitoneal administration co-crystal Form A.

Results are shown in FIGS. 4 and 5.

These data indicate that the co-crystal Form A has increased efficacy and potency compared with psilocybin.

Example 4

$Ca^{2+}$ Release Assay

Cell Culture—AequoScreen™ Chinese hamster ovary (CHO)-K1 cells stably expressing human 5HT2A or 5HT2B (h5HT2A, h5HT2B) were maintained at 37° C., 5% $CO_2$ in F-12 DMEM containing 1 mM L-glutamine, 10% FBS, and 1% Pen/Strep.

$Ca^{2+}$ Assay—Release of $Ca^{2+}$ into the cellular cytosol upon GPCR-dependent activation of $Ga_{q/11}$ was determined using the AequoScreen™ assay in CHO-K1 cells stably expressing h5HT2A or h5HT2B. In addition to the receptor of choice, the AequoScreen™ cell lines stably express the photoprotein apoaequorin, which possesses three $Ca^{2+}$ binding sites. Upon binding $Ca^{2+}$, apoaequorin becomes activated to aequorin and converts coelenterazine to coelenteramide, $CO_2$, and light. Light production is therefore directly proportional to the release of $Ca^{2+}$ from intracellular stores upon GPCR activation. Cells were seeded into flat bottom, white bottom, white wall, poly-D-lysine coated 96-well plates (20,000 cells/well) and incubated overnight in Opti-MEM containing 1% FBS at 37° C. and 5% $CO_2$. Following this, Opti-MEM media was removed and replaced with fresh Opti-MEM containing 5 µM coelenterazine h (Promega, Madison, WI) and 1% FBS (final volume 50 µL) and cells were incubated at 25° C. for 4 h. After these 4 h, cells were treated with 50 µL 2× concentrated ligand solutions to achieve the concentrations indicated and centrifuged at 1,000×g for 1 min at room temperature. Chemiluminescence was then immediately measured on a Cytation5 plate reader (top read, gain 200, integration time 10,000 msec). All experiments included a vehicle control (5% DMSO) and LSD was included in all experiments as a reference agonist.

Figure 6:
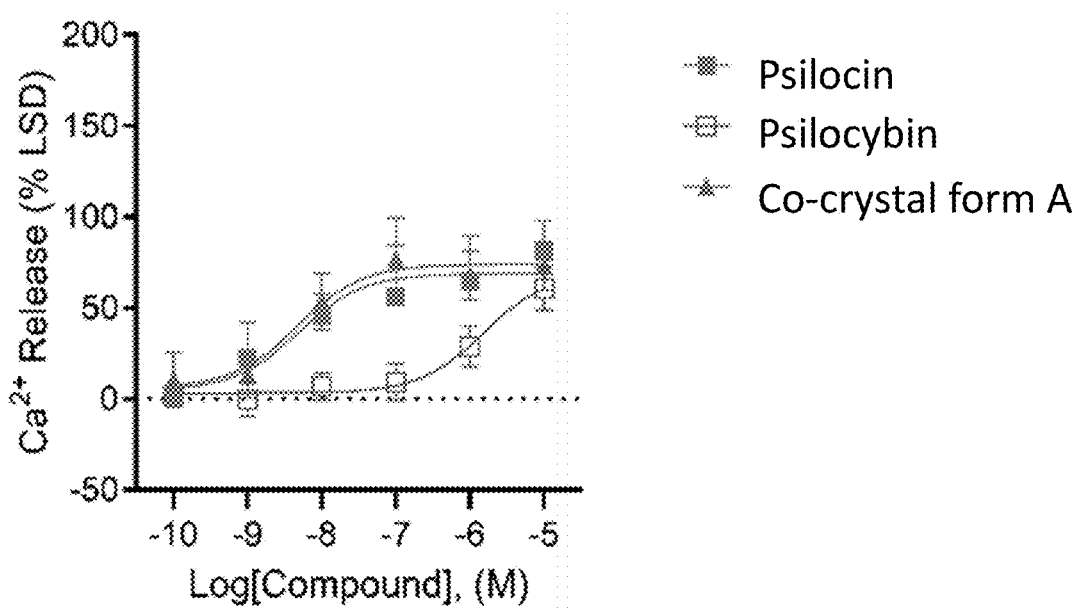
FIG. 6 shows $Ca^{2+}$ release after treatment with psilocin, psilocybin, and co-crystal Form A.

Psilocin displayed high potency for 5-HT2A (FIG. 6, Table 3). Psilocybin displayed lower potency for 5-HT2A than psilocin. Co-crystal Form A's activity closely resembled psilocin with potency and efficacy values that were not different from psilocin. These findings indicate that the co-crystal of psilocin and psilocybin has different and unexpected properties compared to psilocybin or psilocin alone.

42

TABLE 3

| | 5-HT2A-dependent $Ca^{2+}$ release | | |
|---|---|---|---|
| Compound | Potency (nM) ($pEC_{50}$ ± S.E.M.) | Efficacy (% ± S.E.M.) | n |
| LSD | 25 nM (7.6 ± 0.19) | 82 ± 4.7% | 51 |
| Serotonin (5HT) | 37 nM (7.4 ± 0.66) | 110 ± 25% | 16 |
| Psilocin | 4.9 nM (8.3 ± 0.66) | 69 ± 12% | 12 |
| Psilocybin | 1,500 nM (5.8 ± 0.38)**,^^ | 69 ± 15% | 18 |
| Co-crystal Form A | 4.8 nM (8.3 ± 0.52) | 74 ± 10% | 17 |

**$p < 0.01$ compared to LSD, ^^$p < 0.01$ compared to psilocin

Example 5

Neuroplasticity: βarrestin2 Recruitment Assay

Cell Culture—CHO-K1 cells were transfected with either NanoBit™ smBIT h5HT2A plasmids and lgBiT βarrestin2 plasmid. When h5HT2A and βarrestin2 come into contact with one another the smBiT and lgBiT peptides complement each other to produce a complete NanoBit™ luciferase enzyme. When complete, the enzyme is able to catalyze the breakdown of the molecule coelenterazine to produce light. Emitted light levels are proportional to interactions between receptor and βarrestin2. Cells were maintained at 37° C., 5% $CO_2$ in F-12 DMEM containing 1 mM L-glutamine, 10% FBS, and 1% Pen/Strep. For transfections, CHO-K1 cells were seeded in 6-well plates (500,000 cells per well) and incubated overnight in standard media as described above. Following overnight incubation, the cells were transfected with 1 µg of both the h5HT2A and the βarr2 NanoBiT plasmids. Transfections were carried out using Lipofectamine 3000 (Fisher Scientific, Ottawa, ON), according to the manufacturer's protocol in Opti-MEM media containing 1% FBS. After 24 h, the cells were seeded in poly-D-lysine coated 96-well plates at a density of 20,000 cells per well and incubated overnight maintained at 37° C., 5% $CO_2$ in F-12 DMEM containing 1 mM L-glutamine, 10% FBS, and 1% Pen/Strep prior to use.

βarrestin2 assay—After seeding at 20,000 cells/well in flat bottom, white bottom, white wall, poly-D-lysine coated 96-well plates, transfected CHO-K1 cells were rinsed twice with Hank's buffered salt solution (HBSS), and 100 µL of HBSS was added to each of the wells. To this, 25 µL of Nano-Glo Live Cell Substrate was added (diluted 1/20 in the Nano-Glo LCS Dilution buffer, according to the manufacturer's protocol), and the plate was transferred to a Cytation5 plate reader. After a 1 h equilibration phase, 10 µL of the 13.5× concentrated ligand solutions were added, and the luminescent signal was monitored continuously for 2 h (top read, gain 200, integration time 10,000 msec). Each experiment was performed in triplicate with the number of independent experiments per compound listed in tables found in this report's Results section. Luminescent data for the first 30 min were used to automatically generate a time-by-luminescence area under the curve (AUC) for each concentration of compound. AUC data were then used for subsequent analyses. All experiments included a vehicle control (5% DMSO) and lysergic acid diethylamide (LSD) was included in all experiments as a reference agonist.

Figure 7:
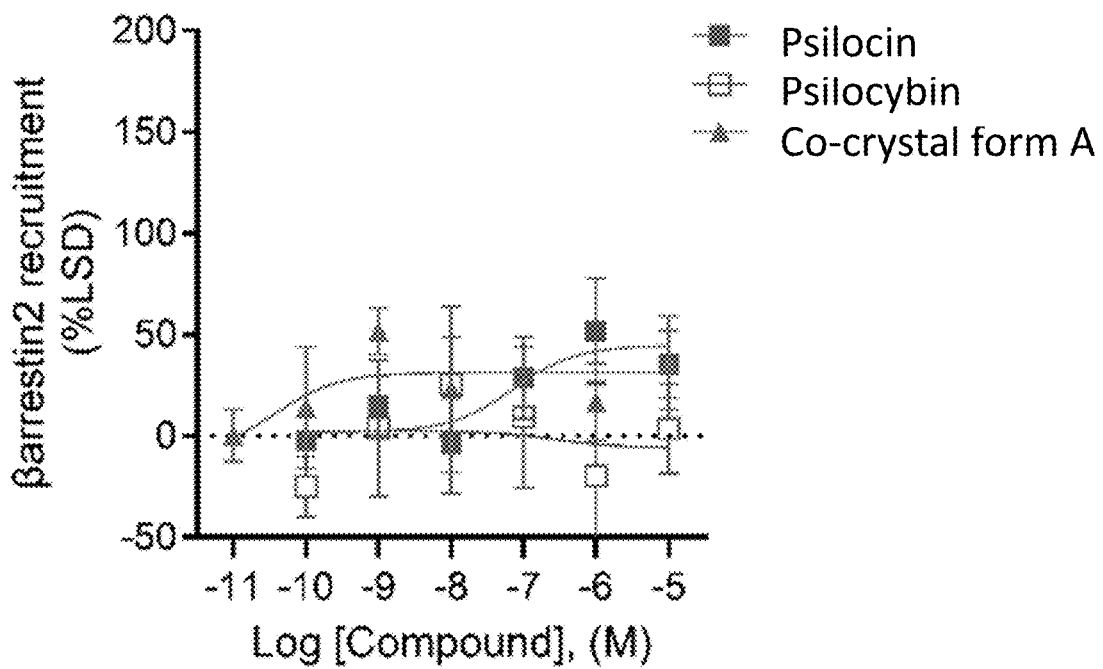
FIG. 7 shows βarrestin2 recruitment after treatment with psilocin, psilocybin, and co-crystal Form A.

Psilocin displayed intermediate potency for 5-HT2A (FIG. 7, Table 4). Psilocybin did not display clear activity for 5-HT2A. Co-crystal Form A's was more potent and equally as efficacious as psilocin.

TABLE 4

| | 5-HT2A-dependent βarrestin2 recruitment | | |
|---|---|---|---|
| Compound | Potency (nM) (pEC$_{50}$ ± S.E.M.) | Efficacy (% ± S.E.M.) | n |
| LSD | 11 nM (7.9 ± 0.20) | 83 ± 4.7% | 41 |
| Serotonin (5HT) | 25 nM (7.6 ± 1.4) | 37 ± 16%* | 9 |
| Psilocin | 71 nM (7.1 ± 0.93) | 45 ± 15%* | 12 |
| Psilocybin | not converged | 3.7 ± 22%**** | 7 |
| Co-crystal Form A | 0.39 nM (10 ± 2.2) | 31 ± 12% | 3 |

****p < 0.0001, *p < 0.05 compared to LSD

Example 6

BDNF Expression, Neuronal Growth, and Neuronal Proliferation

Human Cortical Brain Organoid Culturing Conditions. Human induced pluripotent stem cells (hiPSCs) were cultured in 6-well tissue culture plates coated with Matrigel. First, the cells were incubated with DMEM/F-12 media containing Dispase for 7 minutes, followed by two washes of DMEM/F-12. Cells were scraped, centrifuged, and the pellet was resuspended in mTESR1 medium. Resuspended hiPSCs were re-plated and allowed to grow in mTESR1 for 48 hours. Embryoid bodies (EB) were generated by dissociating hiPSCs and incubating with Accutase for 1 minute prior to transfer to a conical tube for centrifugation in DMEM/F-12 medium. The cell suspension was diluted to a concentration of 60,000 live cells/ml and Y-27632 and 5% (v/v) heat-inactivated FBS was added. 150 µL of cell suspension was added to U-bottom ultra-low-attachment 96-well plates and placed at 37 C. On day 2, neural induction medium was added to each well. On days 4, 6, and 8, fresh neural induction media was added. On day 10 ~8 EBs were transferred to each well in an ultra-low-attachment 6-well plate. Neural differentiation medium was added to each well and they were placed on an orbital shaker inside a 37° C. incubator at 80 rpm. On days 12, 14, and 16, medium was aspirated, and fresh neural differentiation medium added. On day 18, neural differentiation medium was added to each well. Neural differentiation medium was then changed every 4 days until assay commencement.

Mouse Breeding & Drug Injection Details. 14-week-old female CD1 mice, with an average weight of 23 g, were injected intraperitoneally once per day for 14 consecutive days with the following drug treatments: 1) vehicle (230 µL) and 2) Co-crystal Form A (0.3 mg/kg). A solution of 0.67% DMSO in PBS was used as the vehicle. For immunohistochemistry sampling, EdU (5-Ethynyl-2'-deoxyuridine, Lumiprobe, 100 µg/g) was injected together with the drugs for the first 7 days. On the day following the 14-day treatment period, the brains of the mice were dissected for subsequent analyses, including immunohistochemistry and electrophysiology (E-phys).

Figure 8:
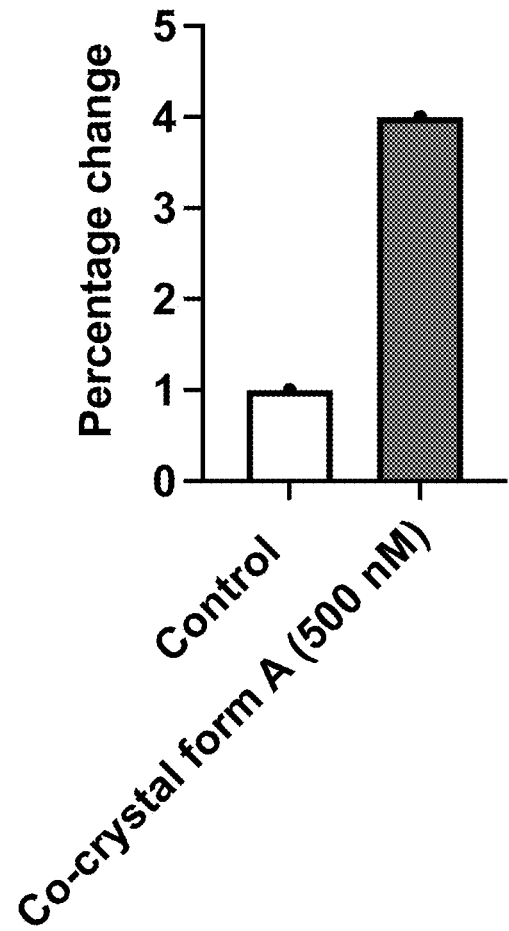
FIG. 8 shows induction of BDNF gene expression at 6 hours after administration of co-crystal Form A (500 nM) in 4-month old brain organoids.

Quantitative Polymerase Chain Reaction (qPCR). To measure BDNF expression Trizol was used to extract RNA from the organoids. Initially, one organoid was placed in a 1.5 mL tube and 250 µL of Trizol was added and the tissue was homogenized with a plastic stirrer. 62.5 µl of Choloroform was added and the tube was inverted and left at room temperature for 2 minutes and then centrifuged at 12,000×g for 15 minutes at 4° C. Post-centrifugation, the aqueous middle layer was carefully transferred to a fresh 1.5 mL tube, and 1:1 2-propanol was added. The tube was again centrifuged at 12,000×g for 20 minutes, the supernatant was then poured off and the tube was left to dry. 1000 µL of 70% ethanol was added and the tube was repetitively inverted to mix and was then centrifuged at 4 C for 5 minutes at 12,000×g, the supernatant was then poured off. Following 15 minutes of air drying, the pellet was resuspended in 20 µL of sterile water and concentration determined using a Nanodrop machine. Reverse transcription was completed with 1 µg of RNA, 2 µL gDNA wipeout buffer 7×, and the solution was brought to a total volume of 14 µL with the addition of RNA free water. Tubes were incubated at 42 C for 2 minutes and then placed on ice. Each tube then received 1 µL of Reverse Transcriptase (RT), 4 µl of RT buffer, 1 µL of RT primer mix, to bring the total volume to 20 µL mastermix per replicate. Tubes were then incubated at 42° C. for 15 minutes and 3 minutes at 95° C. Qiagen SYBR Green kit was used for qPCR, each well on a 384 well plate received 5 µL SYBR Green, 2.8 µL RNase free water, 0.6 µL of each the forward and reverse primer (housekeeping were Y-WHAZ & GAPDH, target was BDNF), and 1 µl of cDNA. Results are shown in FIG. 8.

Human Cortical Brain Organoid Culturing Conditions. Adult male and female C57BL/6 mice aged 8-10 weeks were treated with 0.3 mg/kg or 3 mg/kg of each compound via oral gavage (p.o.). and euthanized to collect whole brain 10 min after oral administration.

Figure 9:
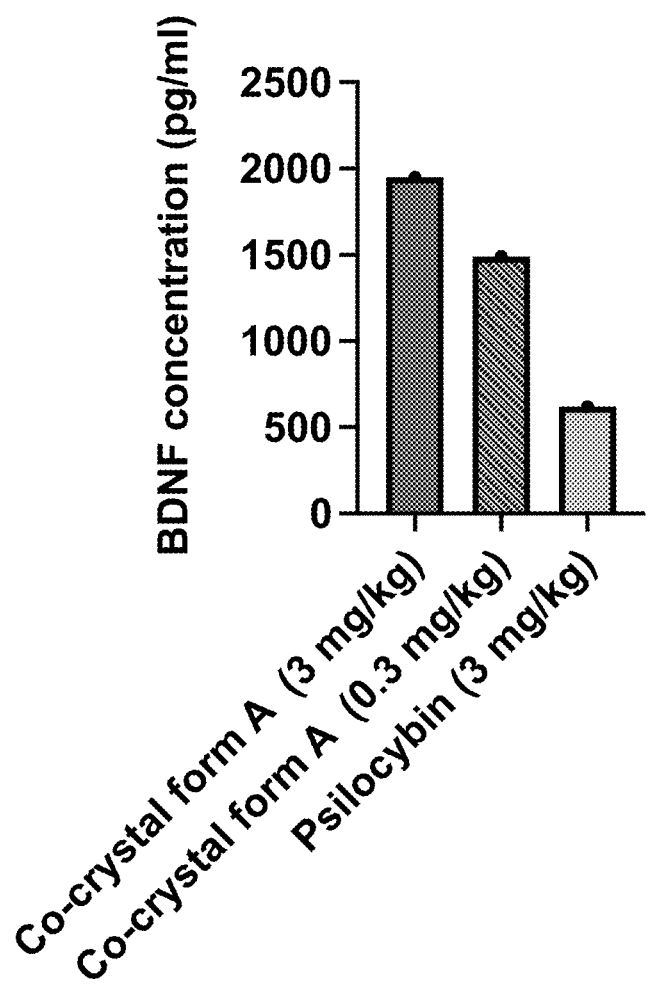
FIG. 9 shows brain BDNF levels 10 minutes after oral administration of co-crystal Form A or psilocybin.

BDNF Enzyme-linked Immunosorbent Assay. The BDNF enzyme-linked immunosorbent assay (ELISA) was used to quantify total BDNF levels in whole brain homogenate from mice using the standard operating protocol detailed by the product manufacturer. Results are shown in FIG. 9.

These results demonstrate significant increases in BDNF levels in brain within 10 minutes of oral administration, in marked contrast to equivalent doses of Psilocybin.

Brain Organoid Neurite Outgrowth Assay. 6-month-old cortical organoids (CO) & median ganglion eminence organoids (MGEO) were fused to become an assembloid and were treated for 10 days with the following drug conditions: 1) vehicle, 2) Co-crystal Form A (500 nM). A solution of 0.1% DMSO in growth media was used as the vehicle. The media were replaced daily with fresh media containing the drugs. After the 10-day drug treatment, 20 mm×20 mm square cover glasses on each well of a 6-well plate were coated with 1% Geltrex in DMEM/F12+Glutamax for 2 hours at room temperature. The coated plates were then washed with 2 ml of growth media, and 3 ml of warmed fresh growth media was added to each well. Following plate preparation, the drug-treated organoids were sliced 9 times using surgical blades and transferred onto the Geltrex-coated cover glasses in the 6-well plates. The plates were gently swirled to evenly distribute the organoid fragments. The organoid fragments were incubated undisturbed for 3 days to allow attachment and neurite growth. After 3 days of incubation, the attached organoid fragments were washed twice with 3 mL of PBS and fixed with 3 mL of 4% paraformaldehyde in PBS for 1 hour at room temperature. The fixed neurite outgrowth samples were washed three times with 3 ml of PBS and then permeabilized with 3 ml of 0.1% Triton X-100 in PBS (PBT) for 10 minutes. The permeabilized samples were subsequently subjected to immunostaining.

Figure 10:
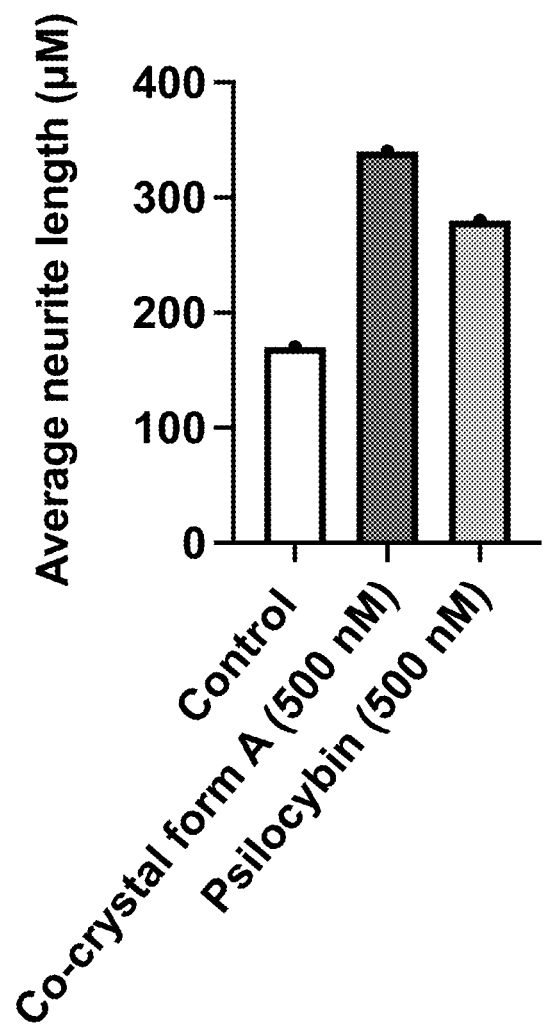
FIG. 10 shows increased neuronal growth as measured by average neurite length at 6 hours after administration of co-crystal Form A (500 nM) in 4-month old brain organoids.
Figure 11:
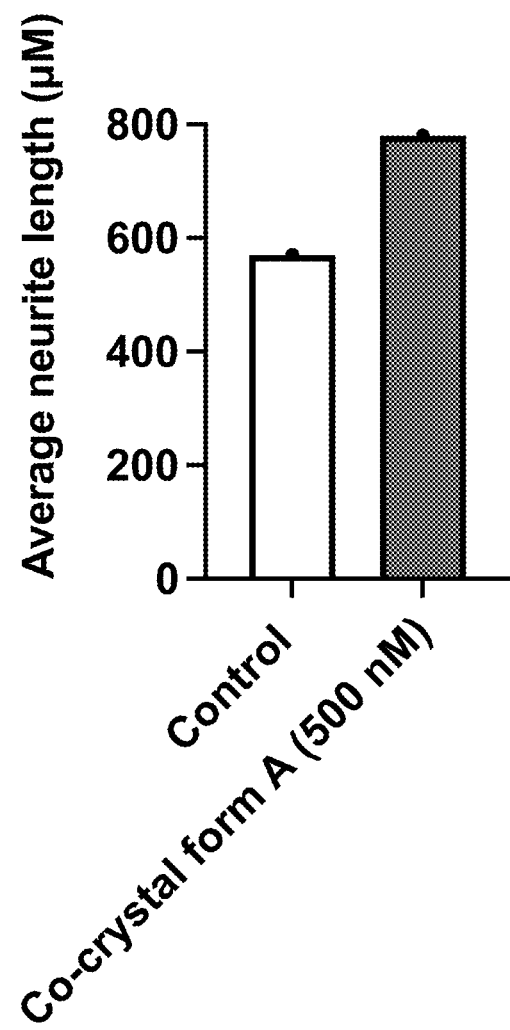
FIG. 11 shows increased neuronal growth as measured by average neurite length at 6 hours after administration of co-crystal Form A (500 nM) daily for 10 days in 6-month old brain organoids.
Figure 12:
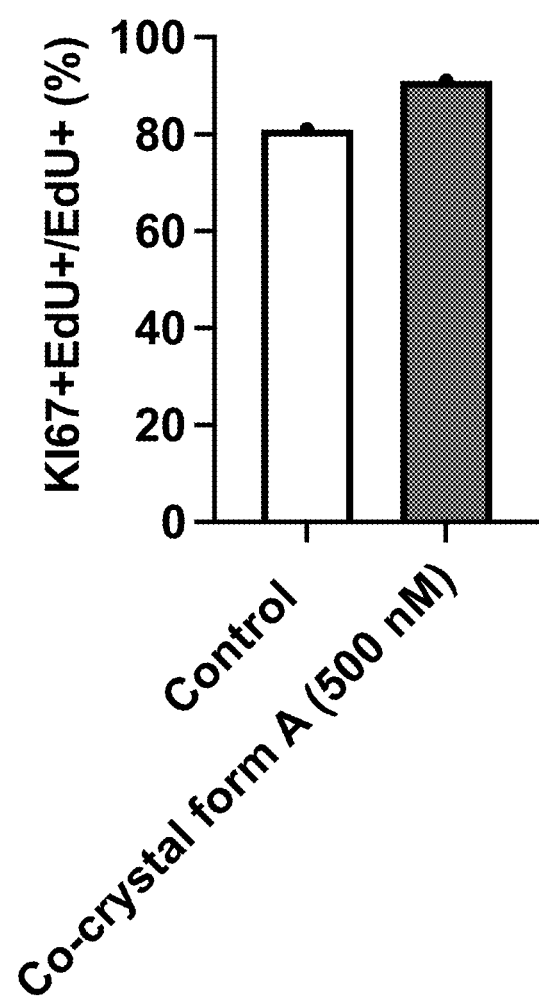
FIG. 12 shows the increased neuronal proliferation as measured at 6 hours after administration of co-crystal Form A (500 nM) daily for 10 days in 6-month old brain organoids.
Figure 13:
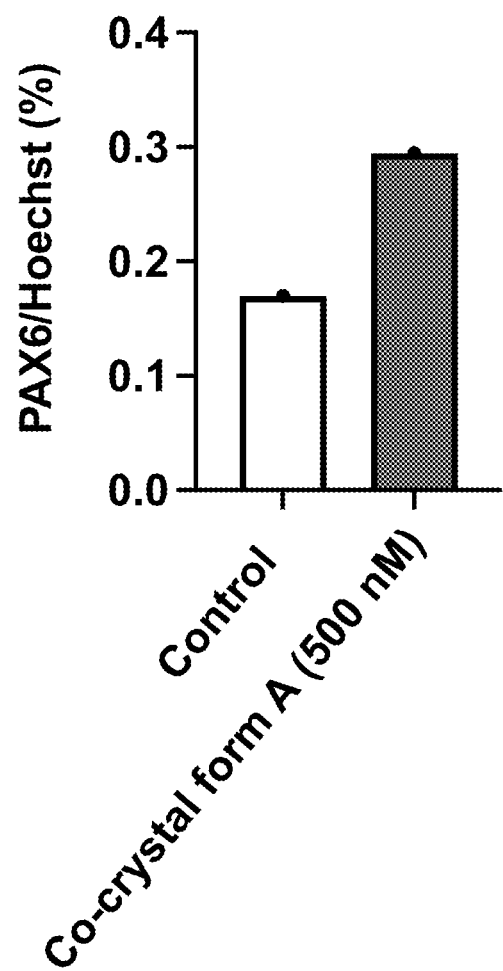
FIG. 13 shows increased number of progenitor neuronal cells at 6 hours after administration of co-crystal Form A (500 nM) daily for 10 days in 6-month old brain organoids.
Figure 14A:
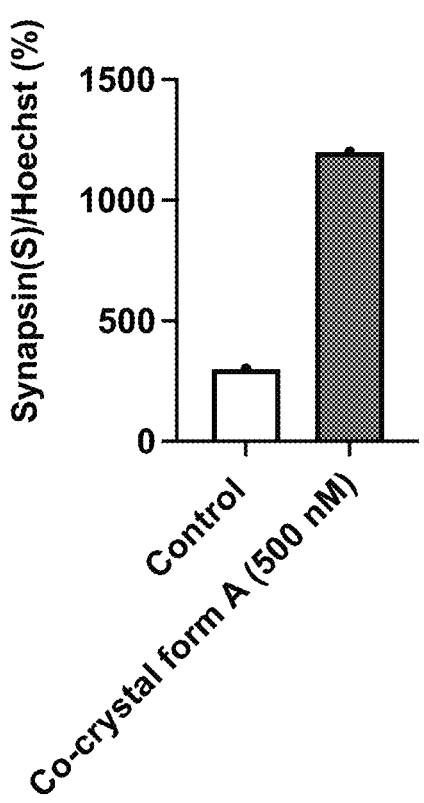
FIGS. 14A-C show increased number of synapses (small synapses (14A), medium synapses (14B), and large synapses (14C)) at 6 hours after administration of co-crystal Form A (500 nM) daily for 10 days in 6-month brain organoids.
Figure 14B:
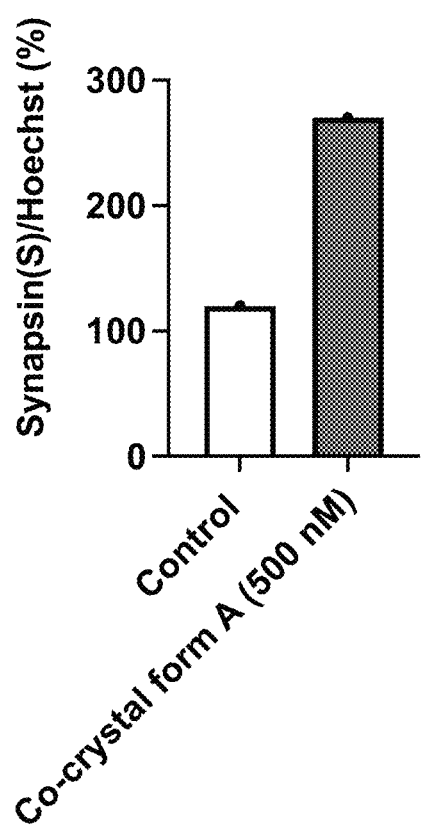
Figure 14C:
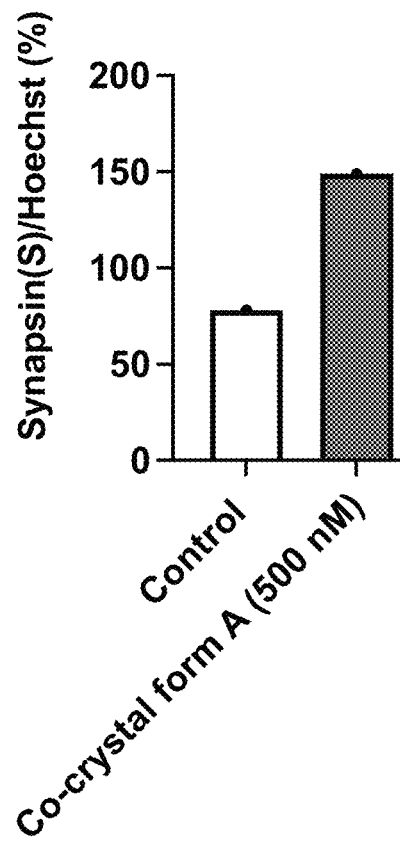
Figure 15:
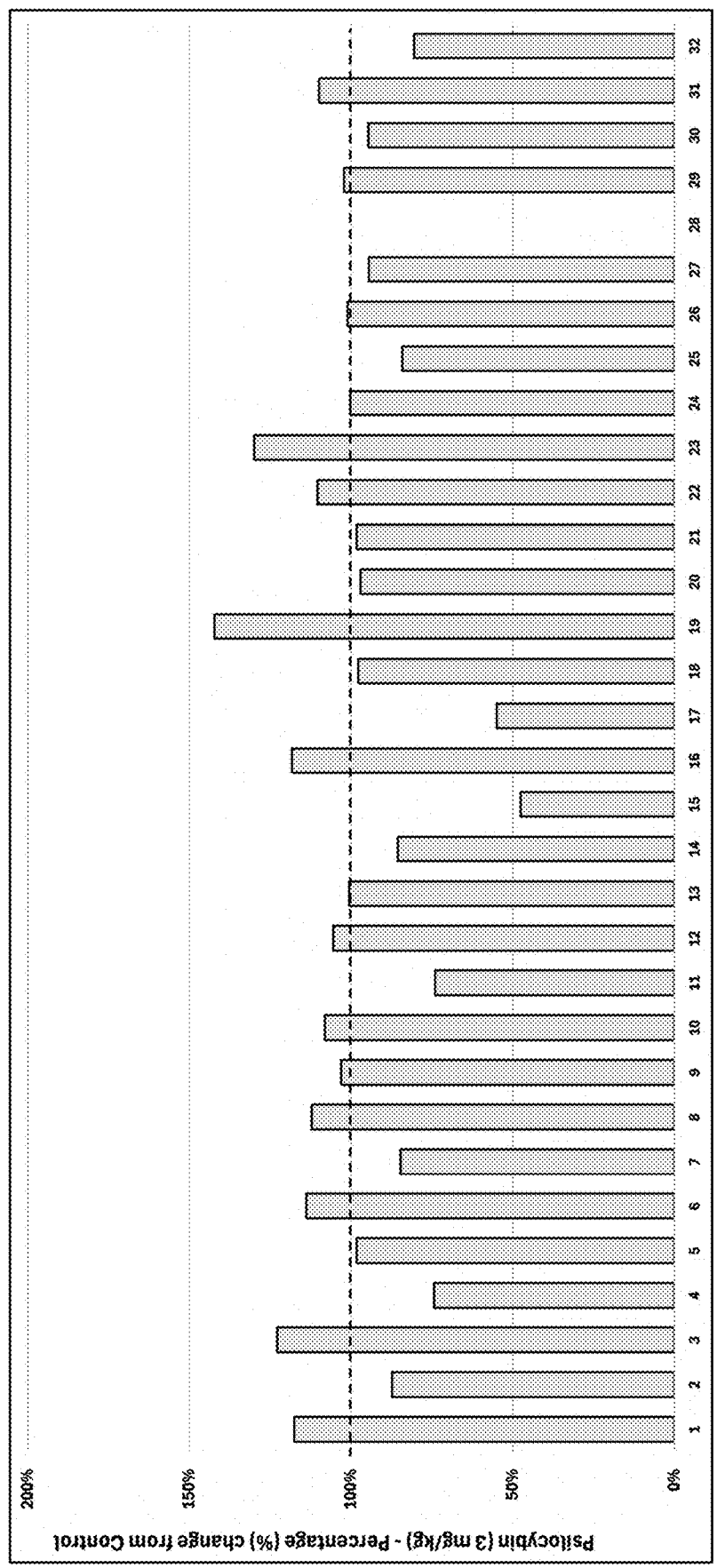
FIG. 15 shows the levels of various cytokine biomarkers of neuroinflammation 60 minutes after oral administration of psilocybin (3 mg/kg).
Figure 16:
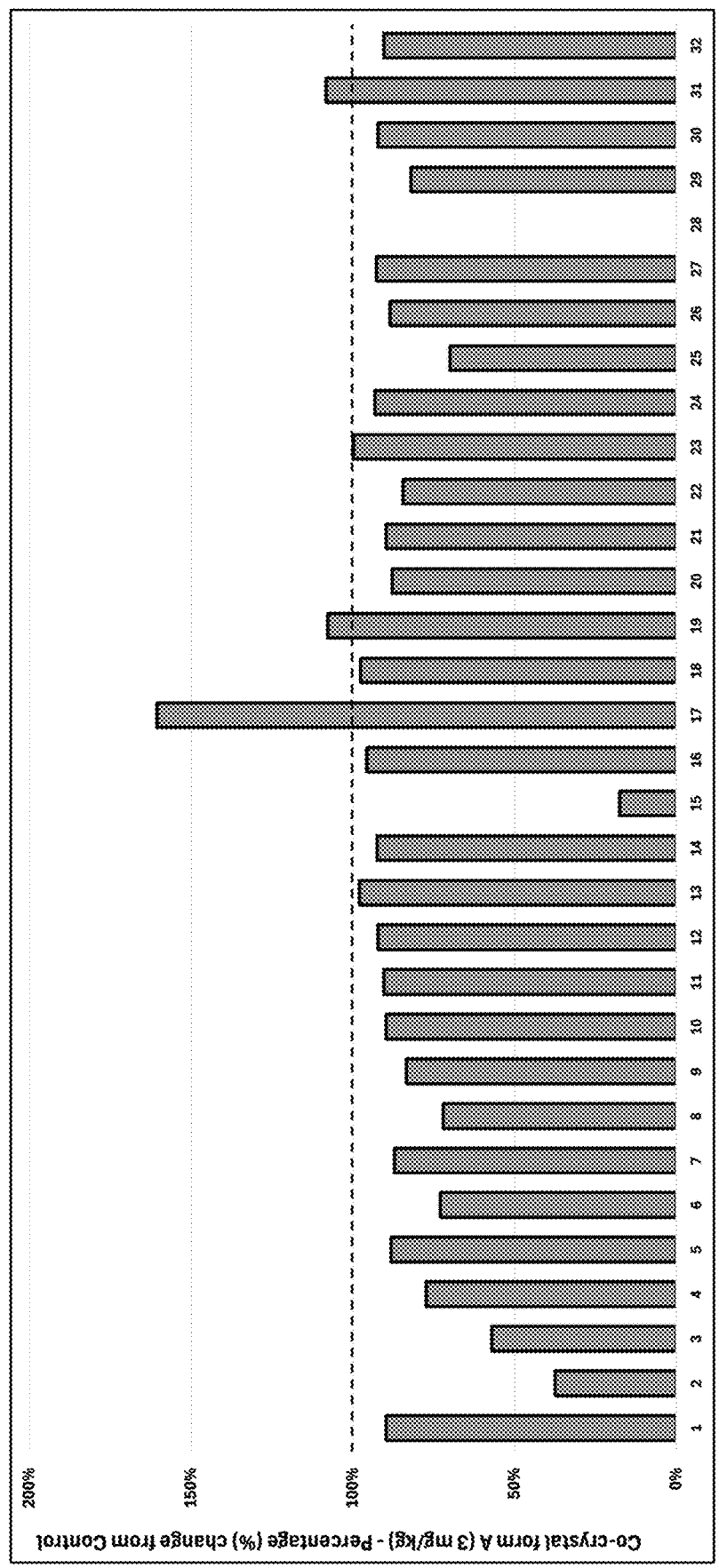
FIG. 16 shows the levels of various cytokine biomarkers of neuroinflammation 60 minutes after oral administration of co-crystal Form A (3 mg/kg).
Figure 17:
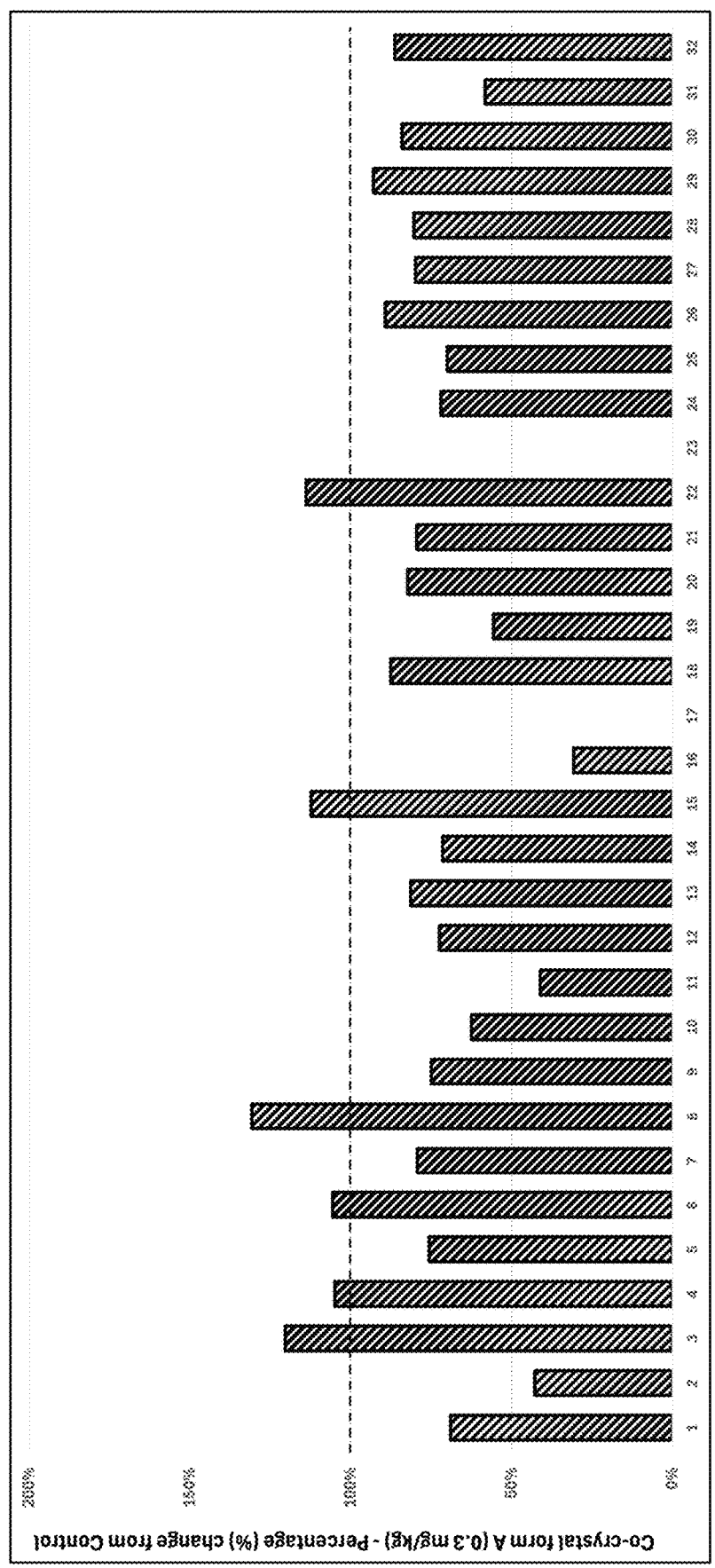
FIG. 17 shows the levels of various cytokine biomarkers of neuroinflammation 60 minutes after oral administration of co-crystal Form A (0.3 mg/kg) daily for 21 days.
Figure 18:
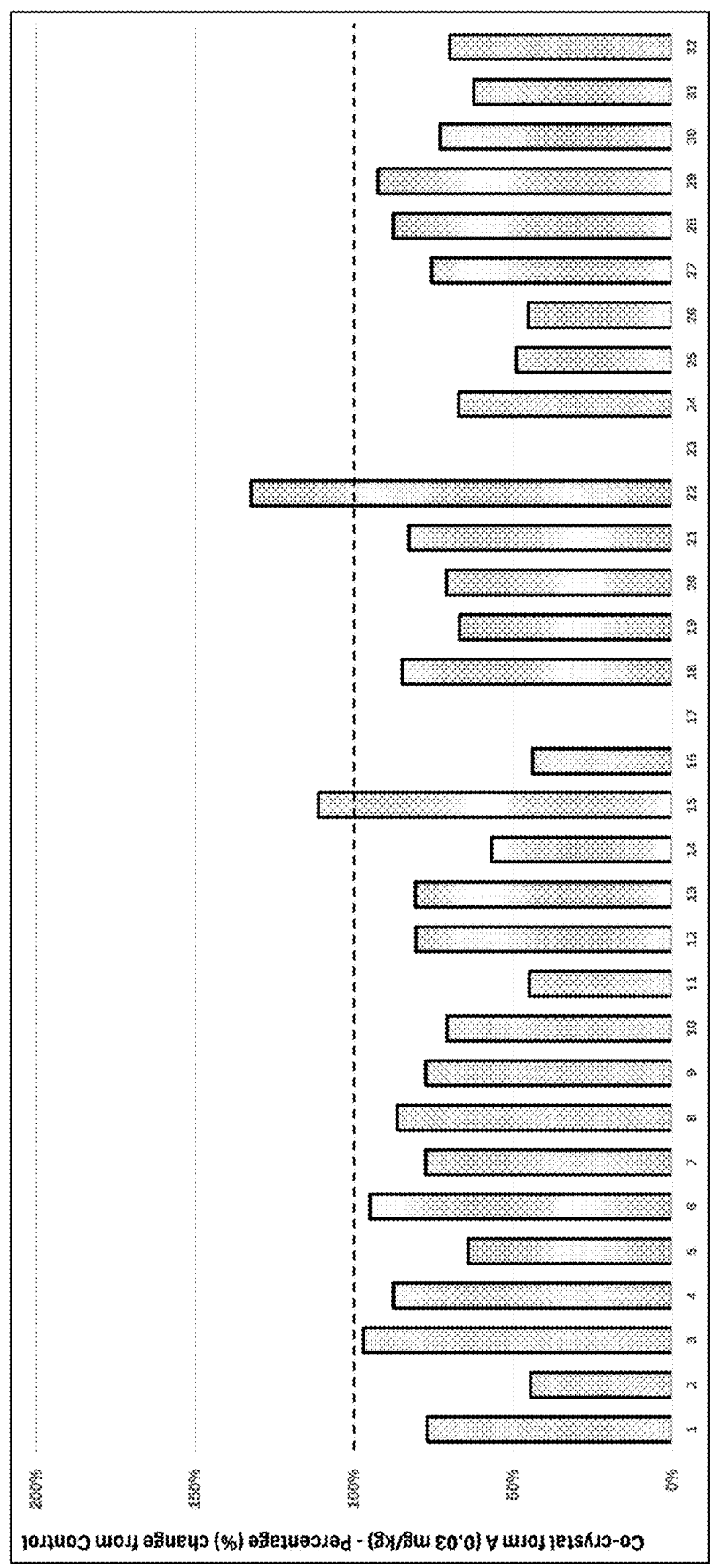
FIG. 18 shows the levels of various cytokine biomarkers of neuroinflammation 60 minutes after oral administration of co-crystal Form A (0.03 mg/kg) daily for 21 days.
Figure 19:
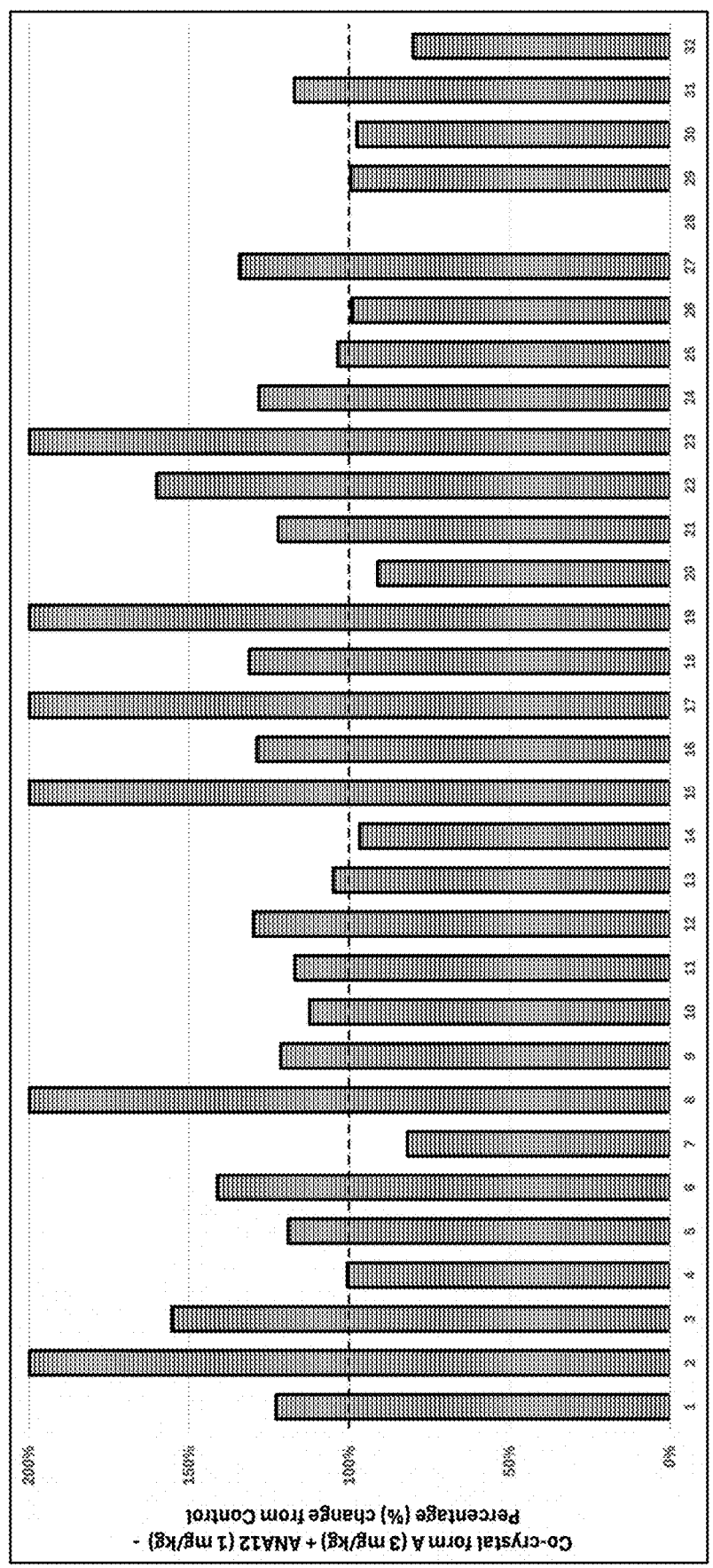
FIG. 19 shows the levels of various cytokine biomarkers of neuroinflammation 60 minutes after oral administration co-administration of co-crystal Form A (3 mg/kg) and ANA12 (1 mg/kg).

For immunostaining, the samples were blocked with 5% normal donkey serum for 1 hour. After blocking, anti-Tuj1 mouse antibody (1:500) in 1 mL of blocking solution was applied overnight at room temperature. Following primary antibody incubation, the samples were washed three times with PBST (0.1% Triton X-100 in PBS). Donkey anti-mouse 488 secondary antibodies (1:500) were then applied for 2 hours at room temperature. After the secondary antibody incubation, the samples were washed three times with PBST and stained with Hoechst 33342 (1:1000 in PBST) for nuclear visualization. After one final wash with PBST, the cover glasses were retrieved and mounted on slide glasses using Aqua-Poly/Mount. Neurite images were obtained using a Zeiss Imager.M2 microscope, and the analysis was performed using Fiji (ImageJ 1.54f) software. Results are shown in FIGS. 10 and 11.

Immunohistochemistry (IHC) & Image Analysis. Sectioned organoids were washed with 1×PBS for 10 minutes on a shaker plate (set to 100), followed by a 0.1% PBT wash. Slides that were not being analyzed for EdU received 1 ml 5% Donkey Serum (diluted in 0.1% PBT) and were incubated at RT for 1 hour. EdU slides (proliferation assay) each received 2× washes of 500 µl of 3% BSA (diluted in PBS) for 2 minutes, then 1 mL of 0.5% triton 100×(diluted in PBS) and were incubated for 20 minutes. Click-iT Plus kit was used for EdU staining and manufacturer instructions were followed. Slides were then washed with 500 µl of 3% BSA (diluted in PBS) and blocked with 5% donkey serum (NDS) for 1 hour. Post-blocking primary antibodies, Ki67 (1:250 in 5% NDS) to EdU slides and both Pax6 (1:250 in 5% NDS) and Synapsin (1:250 in 5% NDS) for non-EdU, were added each with a volume of 200 µL per slide, covered with parafilm, and placed in the 4° C. deli cooler overnight. On day 2, slides were rinsed (4×) with 0.1% PBT for 10 minutes. Rabbit 488 (Rb488) (1:200) was added to label EdU positive cells and Mouse 594 (M594) (1:200) was added to label Ki67 on proliferation assay slides and to label Pax6 and Synapsin on their respective slides. Slides were covered with parafilm and incubated at RT for 2 hours. Slides were rinsed (3×) with 0.1% PBT and then incubated with DAPI (1:1000 in PBS) for 10 minutes at RT. Slides were rinsed (2×) with PBS and coverslips were added. This IHC protocol was used for both mouse and organoid models. Images were gathered via a brightfield microscope, whereby the organoid proliferation, Pax6, and synapsin assays were imaged at 20× and the mouse Pax6 and synapsin were imaged at 63×. Images were obtained on a Zeiss Imager. M2 microscope and ImageJ (Fiji) software was utilized to process the images and count cells based on predetermined fixed parameters set for each model system and counts were graphed using Prism. Results are shown in FIGS. 12, 13, 14A, 14B, and 14C.

These data indicate that, unexpectedly, administration of co-crystal of psilocybin and psilocin increases multiple measures of neuroplasticity. Specifically, increasing levels of BDNF expression, neuronal growth, neuronal proliferation, and the number of synapses.

Example 7

Reduction in Neuroinflammation and TGF-β Level Quantification

Animals—Adult male and female C57BL/6 mice aged 8-10 weeks were treated with vehicle (saline), 3 mg/kg Co-crystal form A, 3 mg/kg psilocybin, 1 mg/kg TrKB inhibitor ANA-12, or a combination of 3 mg/kg Co-crystal form A and 1 mg/kg ANA-12 via oral gavage (p.o.) acutely with blood plasma and brain tissue being collected 1 h post-administration. Alternatively, C57BL/6 mice were treated with vehicle (saline), 0.03 mg/kg Co-crystal form A, 0.3 mg/kg Co-Crystal form A once daily for 21 days via oral gavage and blood plasma and brain tissue being collected 1 h after compound administration on the final (i.e., $21^{st}$ day).

Cytokine Multiplex Discovery Assay—Tissues were immediately frozen and stored at −80° C. prior to shipping. Blood plasma and brain tissue were analyzed with either (1) the Multiplex Analysis of Cytokines Mouse Cytokine 32-Plex Discovery Assay® with plasma or tissue homogenate; or (2) multi-species tumor growth factor (TGF) β 3-plex Discovery Assay® with plasma or tissue homogenate.

Mouse Cytokine 32-Plex Discovery Assay®: This study used Luminex xMAP technology for multiplexed quantification of 32 Mouse cytokines, chemokines, and growth factors. The multiplexing analysis was performed using the Luminex™ 200 system. Thirty-two markers were simultaneously measured in the samples using Eve Technologies' Mouse Cytokine 32-Plex Discovery Assay® according to the manufacturer's protocol. The 32-plex consisted of Eotaxin, G-CSF, GM-CSF, IFNγ, IL-1α, IL-1β, IL-2, IL-3, IL-4, IL-5, IL-6, IL-7, IL-9, IL-10, IL-12 (p40), IL-12 (p70), IL-13, IL-15, IL-17, IP-10, KC, LIF, LIX, MCP-1, M-CSF, MIG, MIP-1α, MIP-1β, MIP-2, RANTES, TNFα, and VEGF. Assay sensitivities of these markers range from 0.3-30.6 pg/mL for the 32-plex. Individual analyte sensitivity values are available through the MilliporeSigma MILLIPLEX® MAP protocol. Data are presented as either percentage relative to the mean vehicle control or as tissue concentrations (pg/mL).

TGF-β 3-Plex Discovery Assay®: This study used Luminex xMAP technology for multiplexed quantification of 3 cytokines: TGF-β1, β2, and β3 in mouse. The multiplexing analysis was performed using the Luminex™ 200 system. Three markers were simultaneously measured in the samples using Eve Technologies' TFG-β 3-Plex Discovery Assay® according to the manufacturer's protocol. The 3-plex consisted of TGF-β1, TGF-β2, and TGF-β3. Assay sensitivities of these markers range from 2.2-6.6 pg/mL for the 3-plex. Individual analyte sensitivity values are available in the MilliporeSigma MILLIPLEX® MAP protocol. Data are presented as either percentage relative to the mean vehicle control or as tissue concentrations (pg/mL).

Results for cytokine biomarkers of neuroinflammation are shown in FIGS. 15-19 with the x-axis numbers represent the following: 1=Eotaxin, 2=G-CSF, 3=GM-CSF, 4=IFNγ, 5=IL-1α, 6=IL-1β, 7=IL-2, 8=IL-3, 9=IL-4, 10=IL-5, 11=IL-6, 12=IL-7, 13=IL-9, 14=IL-10, 15=IL-12p40, 16=IL-12p70, 17=IL-13, 18=IL-15, 19=IL-17, 20=IP-10, 21=KC, 22=LIF, 23=LIX, 24=M-CSF, 25=MCP-1, 26=MIG, 27=MIP-1α, 28=MIP-1β, 29=MIP-2, 30=RANTES, 31=TNFα, and 32=VEGF.

These data indicate that, unexpectedly, the co-crystal Form A decreases expression of brain cytokine biomarkers of neuroinflammation. These indicate that a co-crystal of psilocybin and psilocin reduces multiple cytokine measure of neuroinflammation.

Figure 20:
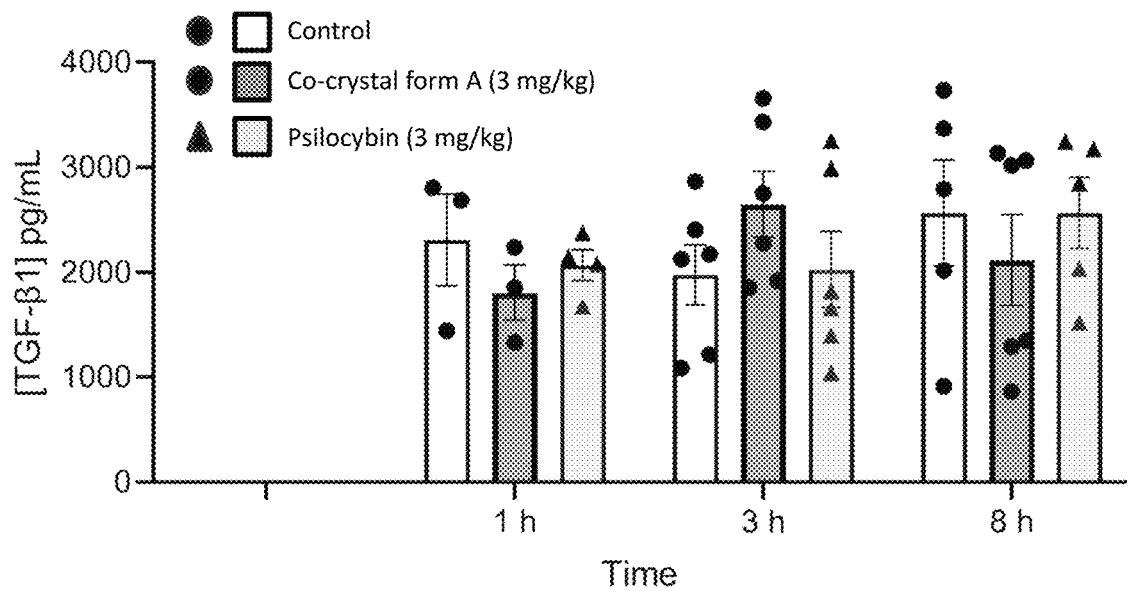
FIG. 20 shows the levels of TGF-β1 at 1 h, 3h, and 8h after administration of co-crystal Form A (3 mg/kg) and psilocybin (3 mg/kg) compared to control.
Figure 21:
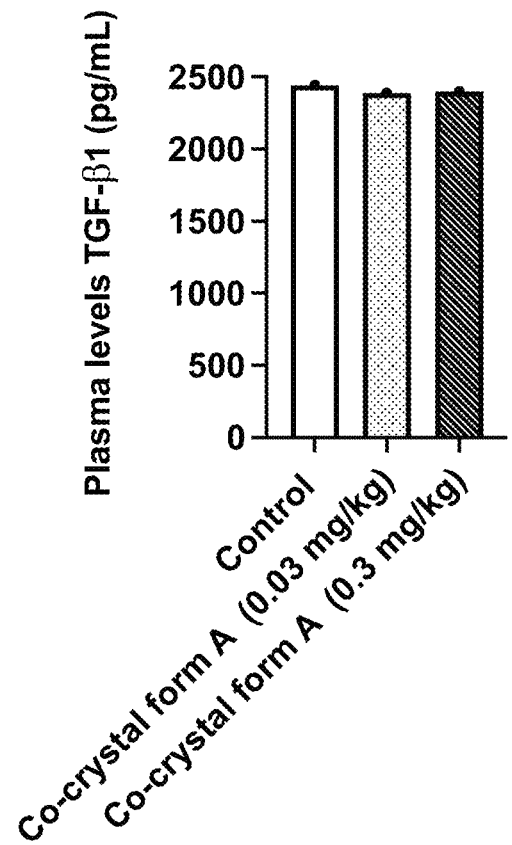
FIG. 21 shows the plasma levels of TGF-β1 after administration of co-crystal Form A (0.03 mg/kg and 0.3 mg/kg) compared to control.

Results for TGF-β1 levels are shown in FIGS. 20 and 21.

These data show that, unexpectedly, the co-crystal Form A does not result in an increase in TGF-β levels in plasma and therefore have a lowered risk of cardiac adverse events. Unlike other drugs which bind to 5-HT2B receptors and are believed to strongly risk having cardiac adverse events, because of this. Activation of 5-HT2B receptors is associated with an increase in plasma levels of TGF-β. The present, unexpected, findings that there is no increase in TGF-β levels strongly suggest that a co-crystal of psilocybin and psilocin may significantly lower risk of causing future cardiac side-effects.

Although the invention has been described with reference to the above examples, it will be understood that modifications and variations are encompassed within the spirit and scope of the invention. Accordingly, the invention is limited only by the following claims.

The invention claimed is:

1. A method of increasing the number of neuronal progenitor cells in a subject in need thereof, comprising administering to the subject a crystalline form of psilocin and psilocybin:

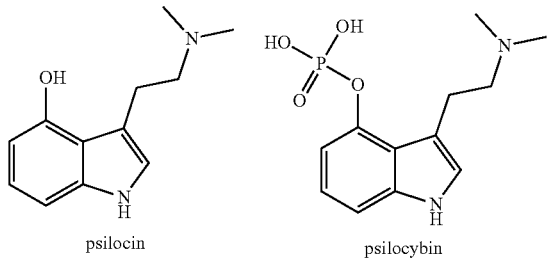

psilocin            psilocybin wherein the crystalline form is co-crystal Form A; and
wherein Form A is characterized by a XRPD pattern comprising a significant peak at a 2θ angle of 10.1° and about 19.16°.

2. A method of increasing BDNF levels in a subject in need thereof, comprising administering to the subject a crystalline form of psilocin and psilocybin:

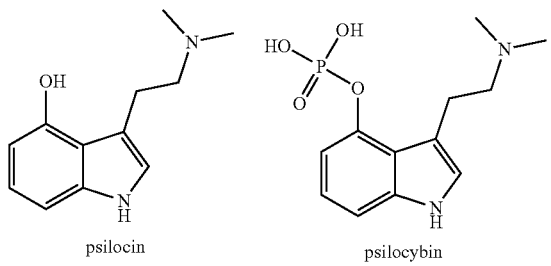

psilocin            psilocybin wherein the crystalline form is co-crystal Form A; and
wherein Form A is characterized by a XRPD pattern comprising a significant peak at a 2θ angle of 10.1° and about 19.16°.

3. The method of claim 1, wherein the number of neuronal progenitor cells is increased by 0.1% to about 10%.

4. The method of claim 2, wherein increasing BDNF levels comprises an increased anti-inflammatory response in the subject.

5. The method of claim 2, wherein BDNF levels are increased by 5% to 150%.

6. The method of claim 4, wherein the anti-inflammatory response comprises a decreased expression of a neuroinflammatory biomarker selected from Eotaxin, G-CSF, GM-CSF, IFNg, IL-la, IL-1b, IL-2, IL-3, IL-4, IL-5, IL-6, IL-7, IL-9, IL-10, IL-12p40, IL-12p70, IL-13, IL-15, IL-17, IP-10, KC, LIF, LIX, M-CSF, MCP-1, MIG, MIP-1α, MIP-1b, MIP-2, RANTES, TNFα, VEGF, or a combination thereof.

7. The method of claim 1, wherein the XRPD pattern further comprises a peak at a 2θ angle of 10.74°, 25.3°, 24.07°, 14.54°, 16.5°, 13.44°, 23.42°, or 8.62°.

8. The method of claim 2, wherein the XRPD pattern further comprises a peak at a 2θ angle of 10.74°, 25.3°, 24.07°, 14.54°, 16.5°, 13.44°, 23.42°, or 8.62°.

9. The method of claim 1, wherein the method decreases the risk of cardiovascular adverse events in response to a 5-HT2B agonist.

10. The method of claim 9, wherein the decreased risk of cardiovascular adverse events comprises decreasing the risk of ventricular heart disease, cardiac fibrosis, or a combination thereof.

11. The method of claim 9, wherein the decreased risk of cardiovascular adverse events comprises maintaining plasma levels of TGF-β1.

12. The method of claim 1, wherein the administering of the crystalline form of psilocin and psilocybin is an acute administration.

13. The method of claim 1, wherein the administering of the crystalline form of psilocin and psilocybin is a chronic administration.

14. The method of claim 2, wherein the method decreases the risk of cardiovascular adverse events in response to a 5-HT2B agonist.

15. The method of claim 14, wherein the decreased risk of cardiovascular adverse events comprises decreasing the risk of ventricular heart disease, cardiac fibrosis, or a combination thereof.

16. The method of claim 14, wherein the decreased risk of cardiovascular adverse events comprises maintaining plasma levels of TGF-β1.

17. The method of claim 2, wherein the administering of the crystalline form of psilocin and psilocybin is an acute administration.

18. The method of claim 2, wherein the administering of the crystalline form of psilocin and psilocybin is a chronic administration.

* * * * *